United States Patent [19]
Kochanek et al.

[11] Patent Number: 5,985,846
[45] Date of Patent: *Nov. 16, 1999

[54] GENE THERAPY FOR MUSCULAR DYSTROPHY

[75] Inventors: Stefan Kochanek; C. Thomas Caskey, both of Houston, Tex.; Kohnosuke Mitani, Tokyo, Japan; Paula R. Clemens, Houston, Tex.

[73] Assignees: Baylor College of Medicine, Houston, Tex.; Howard Hughes Medical Institute, Chevy Chase, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/488,014

[22] Filed: Jun. 7, 1995

[51] Int. Cl.⁶ .............................. A01N 43/04; C12N 15/00
[52] U.S. Cl. ............................................. 514/44; 435/320.1
[58] Field of Search .............................. 435/240.2, 252.3, 435/320.1, 172.3, 91.1, 91.31; 530/350; 536/23.5, 22.1; 514/2, 44

[56] References Cited

U.S. PATENT DOCUMENTS 5,670,488  9/1997  Gregory et al. ......................... 514/44

FOREIGN PATENT DOCUMENTS 9428152   12/1994  WIPO .
WO 9613597  5/1996  WIPO .

OTHER PUBLICATIONS

Mitani et al, "Rescue, Propagation, and Partial Purification of a Helper Virus–Dependent Adenovirus Vector", *Proc. Natl. Acad. Sci. USA*, 92:3854–3858 (1995).
Deuring et al, "An Unusual Symmetric Recombinant Between Adenovirus Type 12 DNA and Human Cell DNA", *Proc. Natl. Acad. Sci. USA*, 78(5):3142–3146 (1981).
Gilardi et al. Expression of human alpha–1–antitrypsin using a recombinant adenovirus vector. FEBS Letters, vol. 267, No. 1, pp. 60–62, Jul. 1990.
Berkner, K. L. Development of Adenovirus Vectors for the Expression of Heterologous Genes. Biotechniques. vol. 6, No. 7, pp. 616–629, 1988.
Karpati et al., Clin. Invest. Med., 17(5), 1994, 499–509.
Amalfitano et al., Am. J. Human Genetics, 57 (4 supp) 1995, A234.
Marshall, Science, 269, 1995, 1050–1055.
Miller et al., FASEB J., 9, 1995, 190–199.
Culver et al., TIG, 1994, 10(5), 174–178.
Hodgson, Exp. Op. Ther. Pat., 5(5), 1995, 459–468.

*Primary Examiner*—Bruce R. Campell
*Assistant Examiner*—Deborah J. R. Clark
*Attorney, Agent, or Firm*—Sughrue, Mion, Zinn, Macpeak & Seas, PLLC

[57] ABSTRACT

A gene transfer vector comprising adenovirus inverted terminal repeats, recombinant adenovirus particles containing the same, a method for producing the same and a method of use of the same to introduce and express a foreign gene in eukaryotic cells, and to treat muscular dystrophy, is disclosed.

2 Claims, 6 Drawing Sheets

FIG. 1

```
CATCATCAAT AATATACCTT ATTTTGGATT GAAGCCAATA TGATAATGAG GGGGTGGAGT

TTGTGACGTG GCGCGGGGCG TGGGAACGGG GCGGGTGACG TAGTAGTGTG GCGGAAGTGT

GATGTTGCAA GTGTGGCGGA ACACATGTAA GCGACGGATG TGGCAAAAGT GACGTTTTTG

GTGTGCGCCG GTGTACACAG GAAGTGACAA TTTTCGCGCG GTTTTAGGCG GATGTTGTAG

TAAATTTGGG CGTAACCGAG CCATTTCGC GGGAAAACTG AATAAGAGGA

AGTGAAATCT GAATAATTTT GTGTTACTCA TAGCGCGTAA TGTTTGTCTA GGGCGGCGGG

ACTTTGACCG TTTACGTGGA GACTCGCCCA GGTGTTTTC TCAGGTGTTT TCCGCGTTCC

GGGTCAAAGT TGGCGTTTTA TTATTATAGT CAGCTGACGT GTAGTGTATT ATACCCGG
```

FIG. 2

CATCATCAAT AATATACCTT ATTTTGGATT GAAGCCAATA TGATAATGAG GGGGTGGAGT

TTGTGACGTG GCGCGGGGCG TGGGAACGGG GCGGGTGACG TAGTAGTGTG GCGGAAGTGT

GATGTTGCAA GTGTGGCGGA ACACATGTAA GCGACGGATG TGGCAAAAGT GACGTTTTTG

GTGTGCGCCG GTGTACACAG GAAGTGACAA TTTTCGCGCC GTTTTAGGCG GATGTTGTAG

TAAAATTTGGG CGTAACCGAG TAAGATGGAC TTTGACCGTT TACGTGGAGA CTCGCCCAGG

TGTTTTTCTC AGGTGTTTTC CGCGTTCCGG GTCAAAGTTG GCGTTTTATT ATTATAGTCA

GCTGACGTGT AGTGTATTTA TACCCGGTCT AGA

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 479 base pairs
      (B) TYPE: nucleic acid
      (C) STRANDEDNESS: single
      (D) TOPOLOGY: linear (ii) MOLECULE TYPE: DNA (iii) HYPOTHETICAL: NO (v) ORIGINAL SOURCE: Adenovirus type 5

(xi) SEQUENCE DESCRIPTION: SEQ ID NO:1:

```
CATCATCAAT AATATACCTT ATTTTGGATT GAAGCCAATA TGATAATGAG GGGGTGGAGT      60

TTGTGACGTG GCGCGGGGCG TGGGAACGGG GCGGGTGACG TAGTAGTGTG GCGGAAGTGT     120

GATGTTGCAA GTGTGGCGGA ACACATGTAA GCGACGGATG TGGCAAAAGT GACGTTTTTG     180

GTGTGCGCCG GTGTACACAG GAAGTGACAA TTTTCGCGCG GTTTTAGGCG GATGTTGTAG     240

TAAATTTGGG CGTAACCGAG TAAGATTTGG CCATTTTCGC GGGAAAACTG AATAAGAGGA     300

AGTGAAATCT GAATAATTTT GTGTTACTCA TAGCGCGTAA TATTTGTCTA GGGCCGCGGG     360

ACTTTGACCG TTTACGTGGA GACTCGCCCA GGTGTTTTTC TCAGGTGTTT TCCGCGTTCC     420

GGGTCAAAGT TGGCGTTTTA TTATTATAGT CAGCTGACGT GTAGTGTATTT ATACCCGG     479
```

(2) INFORMATION FOR SEQ ID NO:2:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: DNA (iii) HYPOTHETICAL: NO (v) ORIGINAL SOURCE: Adenovirus mutant SV5

(xi) SEQUENCE DESCRIPTION: SEQ ID NO:2:

```
CATCATCAAT AATATACCTT ATTTTGGATT GAAGCCAATA TGATAATGAG GGGGTGGAGT      60

TTGTGACGTG GCGCGGGGCG TGGGAACGGG GCGGGTGACG TAGTAGTGTG GCGGAAGTGT     120

GATGTTGCAA GTGTGGCGGA ACACATGTAA GCGACGGATG TGGCAAAAGT GACGTTTTTG     180

GTGTGCGCCG GTGTACACAG GAAGTGACAA TTTTCGCGCG GTTTTAGGCG GATGTTGTAG     240

TAAATTTGGG CGTAACCGAG TAAGATGGAC TTTGACCGTT TACGTGGAGA CTCGCCCAGG     300

TGTTTTCTC AGGTGTTTTC CGCGTTCCGG GTCAAAGTTG GCGTTTTATT ATTATAGTCA     360

GCTGACGTGT AGTGTATTTA TACCCGGTCT AGA                                  393
```

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:3:

```
GGGCCCATCA TCAATAATAT ACCTTATTTT G                                     31
```

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:4:

TGATCTAGAC CGGGTATAAA TACACTACAC GTC					33

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:5:

CCGGGTATAA ATACACTACA CGTC					24

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:6:

GGCGCGCCCC TAGGGGCCGG CCTTAATTAA					30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:7:

ATTTAAATGC CCGCCCGTTT AAACTACGTA					30

GENE THERAPY FOR MUSCULAR DYSTROPHY

The invention described herein was developed with support from the U.S. government under Grant No. NIH 1PO1 HL51.754. The government has certain rights to this invention.

FIELD OF THE INVENTION

The present invention relates to a gene transfer vector comprising adenovirus inverted terminal repeats, and at least one adenovirus packaging signal, recombinant adenovirus particles containing the same; a method for producing the same and a method of use of the same to introduce and express a foreign gene in eukaryotic cells, and to treat muscular dystrophy.

BACKGROUND OF THE INVENTION

I. Adenovirus Vectors

Adenoviruses have attracted increasing attention as expression vectors, especially for human gene therapy (Berkner, *Curr. Top. Microbiol. Immunol.*, 158:39–66 (1992)). This is because the virus particle is relatively stable, and can be prepared as a high titer stock ($10^9$ plaque forming units/ml) without purification. In addition, adenoviruses are useful because they can infect non-replicating cells. Further, adenovirus vectors have been proven safe and effective in humans. However, the following limitations have prevented their general use:

(1) The expression of adenovirus proteins in infected cells is believed to trigger a cellular immune response that precludes long-term expression of the transferred gene (Stratford-Perricaudet et al, *Hum. Gene Ther.*, 1:241 (1990); Ginsberg et al, *Proc. Natl. Acad. Sci., USA*, 88:1651 (1991); Yang et al, *Proc. Natl. Acad. Sci., USA*, 91:4407 (1994); Dai et al, *Proc. Natl. Acad. Sci., USA*, 92:1401 (1995); Jaffe et al, *Nat. Genet.*, 1:372 (1992); Li et al, *Hum. Gene Ther.*, 4:403 (1993); Engelhardt et al, *Hum. Gene Ther.*, 4:759 (1993); Simon et al, *Hum. Gene Ther.*, 4:771 (1993); and Smith et al, *Nat. Genet.*, 5:397 (1993)); and (2) The insert capacity of currently available adenovirus vectors is limited to about 8.0 kb of foreign DNA (Bett et al, *Proc. Natl. Acad. Sci., USA*, 13:8802 (1994)).

Hence, broad application of in vivo gene transfer for the treatment of inherited or acquired diseases requires a substantial improvement of existing systems, or the development of new viral or non-viral vector systems.

A. Reduction of Immunogenicity

In order to reduce the expression of adenovirus proteins, and thus reduce immunogenicity, and in order to prevent viral replication, the current adenovirus vectors have deletions in the E1 and/or E3 regions of the adenovirus genome. All of the other essential viral proteins are encoded by the adenovirus vector itself. E1 proteins can be complemented by culturing the E1 adenoviruses in human 293 cells. The E3 region is dispensable for growth of the virus in vitro.

Recent efforts have been directed at the deletion of additional regions (E2, E4) of the adenovirus genome, which encode early viral functions, in an attempt to further reduce viral gene expression after transduction of the target cells with the adenovirus vector (Engelhardt et al, *Proc. Natl. Acad. Sci., USA*, 91:6196 (1994); Yang et al, *Nature Genet.*, 7:362 (1994); Zhou et al, Gene Therapy and Molecular Medicine, Keystone Symposia on Molecular and Cellular Biology, Steamboat Springs, Colo., Mar. 26–Apr. 1, 1995; Perricaudet et al, *Ibid*; and Finer et al, *Ibid*). To propagate these adenovirus vectors, cell lines have been developed that can provide the deleted functions. However, theoretically, it is very difficult, if not impossible, to provide all of the deleted adenovirus functions by a complementing cell line without substantially compromising the high adenovirus titer, which is currently one of the major advantages of adenovirus vectors.

B. Increasing the Capacity of

Adenoviruses to Carry Foreign Genes The lower packaging limit of adenovirus is unknown. However, the upper packaging limit of Ad5 is approximately 38 kb (Bett et al, *J. Virol.*, 67:5911–5921 (1993)). As a result, adenovirus vectors with deletions of both the E1 and E3 sequences, about 6.0 kb in total, have a capacity for insertion of foreign DNA of up to approximately 8.0 kb.

After repeated passaging of permissive cells infected at a high multiplicity of infection (hereinafter "m.o.i.") with different adenovirus serotypes, subgenomic DNAs preferentially containing the left end of the adenovirus genome are packaged into adenovirus particles, and can be partially separated from wild-type adenovirus particles by cesium chloride (CsCl) density gradient centrifugation (Hammarskjold et al, *Cell*, 20:787–795 (1980)). In addition, after repeated passaging of permissive human KB cells infected at a high m.o.i. with Ad12, hybrid viruses containing symmetrically duplicated chromosomal DNA of the KB cell line flanked by a 700–1150 bp DNA fragment from the left terminus of Ad12 are produced (Deuring et al, *Proc. Natl. Acad. Sci., USA*, 78:3142–3146 (1981); Doerfler, *Curr. Top. Microbiol. Immunol.*, 101:127–193 (1982); and Deuring et al, *Gene*, 26:283–289 (1983)). These hybrid viruses can be partially separated from Ad12 by CsCl equilibrium density gradient, and also can be propagated over years together with Ad12. However, the purity of these particles appears to be very low.

SV40/Ad5 hybrid viruses containing a total of 35 kb which comprise 5.5 copies of the SV40 genome and only 3.5 kb DNA from the left end of Ad5 have also been reported (Gluzman et al, *J. Virol.*, 45:91–103 (1983)). The smallest genome size among the different types of Ad5/SV40 hybrid viruses is about 25 kb (Hassell et al, *J. Mol. Biol.*, 120:209–247 (1978)).

It has recently been determined that the sequences required in cis for replication and packaging of adenovirus DNA comprise less than 500 bp (Grable et al, *J. Virol.*, 64:2047–2056, (1990); and Hearing et al, *J. Virol.*, 61:2555–2558 (1987)).

All of the cis-elements for packaging and replication are contained in 360 bp from the left end of the genome and 103 bp from the right end of the genome (Sussenbach et al, In: *Current Topics in Microbiology and Immunology*, Vol. 109, Doerfler, Ed. Springer-Verlag, Berlin, pp. 53–73 (1983); Tamanoi et al, In: *Current Topics in Microbiology and Immunology*, Vol. 109, Doerfler, Ed. Springer-Verlag, Berlin, pp 75–87 (1983); Hearing et al, supra; and Grable et al, supra).

It was postulated in the present invention that an adenovirus vector could be prepared in which all of the regions of the adenovirus genome were deleted, except for the packaging signal, and the inverted terminal repeats, containing the replication signal. Thus, it was postulated in the present invention that is possible to accommodate up to 37 kb of foreign DNA into defective adenovirus vectors by supplying all of the proteins in trans from a helper virus or cell line. As a result, it was postulated in the present invention that it would be possible to deliver multiple or large genes containing tissue-specific or inducible promoters, as well as marker genes, in one vector, in cis. Such a vector would not encode any viral proteins, and thus would not be toxic or immunogenic to the host. Hence, the above-discussed problem of the immune response of the host arising from expression of viral proteins from the known adenovirus vectors might also be diminished.

Helper-dependent adenovirus vectors encoding the SV40 T antigen have been previously reported (Mansour et al, *Proc. Natl. Acad. Sci., USA*, 82:1359–1363 (1985); and Yamada et al, *Proc. Natl. Acad. Sci., USA*, 82:3567–3571 (1985)). However, these vectors, which were used to overproduce the polyoma T antigens (Mansour et al, supra) and the HSV thymidine kinase gene (Yamada et al, supra), had to be selected for by their growth in monkey cells. The T antigen provides a helper function, which overcomes the block to adenovirus growth in simian cells. However, since the T antigen of the tumor virus, SV40, is able to transform cells to a cancerous state (Hunter, *Sci. Amer.*, 251:70–79 (1994)), it cannot be used in any application in humans.

It was postulated in the present invention, that the use of a selection step could be avoided by the gene transfer vectors of the present invention, and that CsCl centrifugation could be employed to purify the recombinant adenovirus, as well as enrich for the recombinant adenovirus.

II. Muscular Dystrophy

Duchenne muscular dystrophy (DMD) and Becker muscular dystrophy (BMD) are allelic, lethal degenerative muscle diseases with an incidence of 1:3500 male births (Clemens et al, In: *Current Neurology, Appel*, Ed., Mosby-Year Book, Chicago, Ill., Vol. 14, pp. 29–54 (1994)). In DMD, mutations in the dystrophin gene usually result in the absence of dystrophin, a cytoskeletal protein in skeletal and cardiac muscle. In BMD, dystrophin is usually expressed in muscle, but at a reduced level and/or as a shorter, internally deleted form, resulting in a milder phenotype. No effective treatment is available for DMD or BMD at this time.

Currently, viral vector gene delivery represents the most promising technology for gene transfer into muscle in vivo. However, because of the limited capacity of first-generation adenovirus vectors, only a truncated form of the dystrophin cDNA, derived from a patient with mild BMD, has been used in the initial studies of adenovirus vector-mediated gene transfer for DMD (Ragot et al, *Nature*, 361:647 (1993)).

Thus, there has been a need in the art to develop vectors which have a greater capacity for insertions so as to allow for the delivery of full-length dystrophin cDNA.

SUMMARY OF THE INVENTION

An object of the present invention is to provide a gene transfer vector that does not induce a host cellular immune response against expressed viral proteins.

An additional object of the present invention is to provide a gene transfer vector that can carry about 36 kb of foreign DNA.

Still another object of the present invention is to provide recombinant adenovirus particles which have encapsidated therein said gene transfer vectors, as well as a method for isolating said recombinant adenovirus particles.

Yet another object of the present invention is to provide a method for introducing and expressing foreign genes in eukaryotic cells.

A further object of the present invention is to provide a method for treatment of muscular dystrophy.

These and other objects, which will be apparent from the detailed description of the invention provided hereinafter, have been met in one embodiment, by a gene transfer vector comprising, in 5' to 3' orientation, the following elements:

(i) a first adenovirus inverted terminal repeat, (ii) a foreign gene, and (iii) a second adenovirus inverted terminal repeat, wherein one or both of element (i) and element (iii) additionally comprise an adenovirus packaging signal.

BRIEF DESCRIPTION OF THE DRAWINGS

FIG. 1 shows the DNA sequence of a DNA fragment containing the inverted terminal repeat and full-length packaging signal of Ad5 (SEQ ID NO:1). In FIG. 1, the inverted terminal repeat (nucleotides 1–103) is in italics, and the 5 elements constituting the packaging signal (nucleotides 194–358) are in bold.

FIG. 2 shows the DNA sequence of a DNA fragment containing the inverted terminal repeat and impaired packaging signal of adenovirus mutant SV5, wherein 3 of the 5 packaging signals are removed (SEQ. ID NO:2). In FIG. 2, the inverted terminal repeat is in italics, the retained 2 elements constituting the impaired packaging signal are in bold, and the XbaI site used for ligation to adenovirus DNA extending from nucleotide 1339 to the right end of FG140 virus is underlined.

DETAILED DESCRIPTION OF THE INVENTION

Figure 3A:
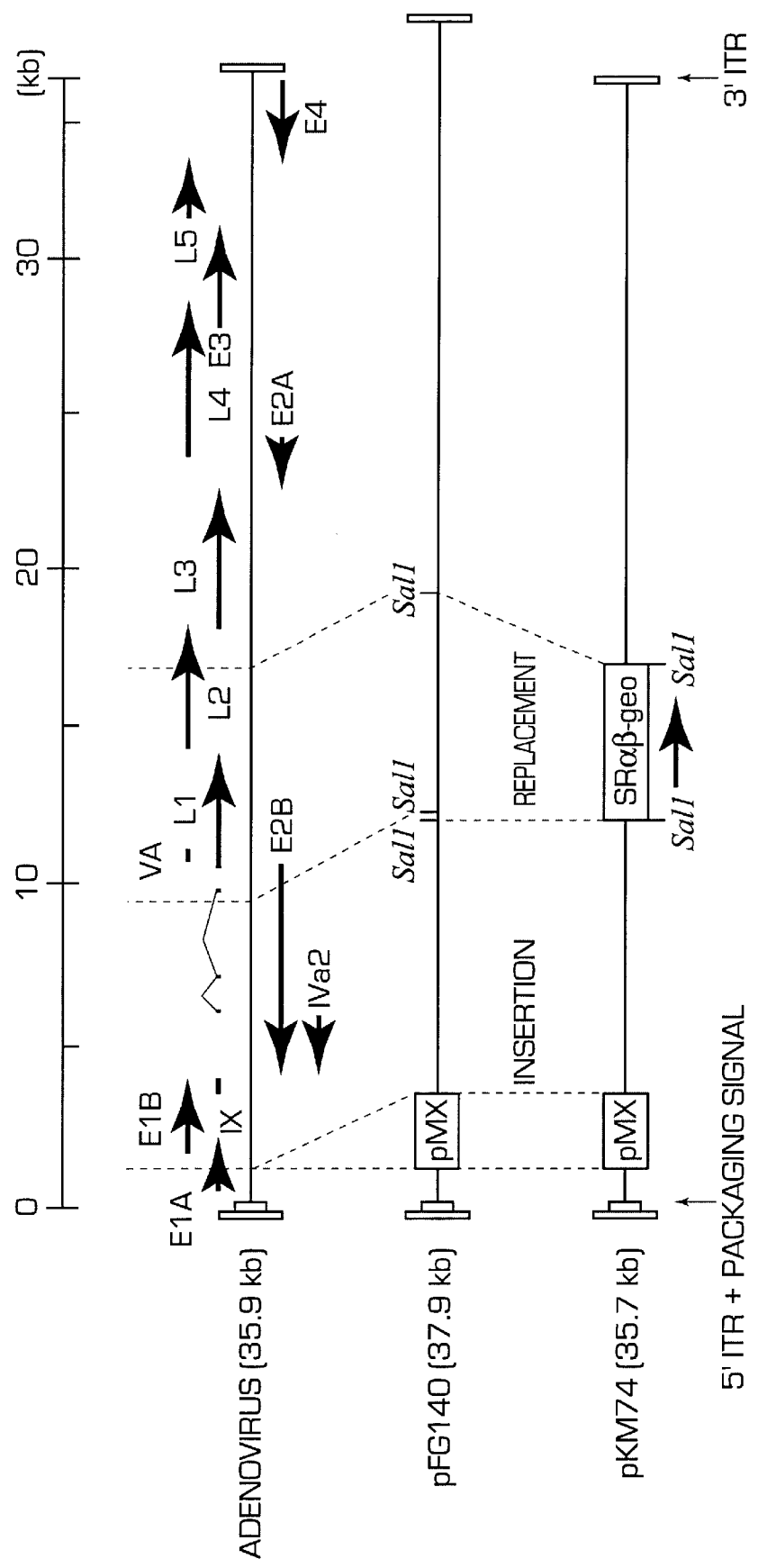
FIGS. 3A and 3B show gene transfer vector pKM74 in its linearized form compared to parental pFG140 and wild-type Ad genomic DNA (FIG. 3A), and in its circularized form (FIG. 3B). This plasmid contains a left end adenovirus inverted terminal repeat (ITR) and packaging signal, and a right end adenovirus inverted terminal repeat (ITR). The foreign gene, β-geo, which is a fusion of the neo gene and the β-gal gene, is present in between the inverted terminal repeats. The transcription map of adenoviruses is also shown by thick arrows.

As discussed above, in one embodiment, the present invention relates to a gene transfer vector comprising, in 5' to 3' orientation, the following elements:

(i) a first adenovirus inverted terminal repeat, (ii) a foreign gene, and (iii) a second adenovirus inverted terminal repeat, wherein one or both of element (i) and element (iii) additionally comprise an adenovirus packaging signal.

The inverted terminal repeats constitute the adenovirus origin of replication.

The particular adenovirus serotype employed in the present invention from which the inverted terminal repeats are derived or based upon which the DNA sequence of the inverted terminal repeats are synthesized, is not: critical. Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: *Adenovirus DNA*, Doerfler, Ed., Martinus Nijhoff Publishing, Boston, pp. 408–441 (1986)), as well as any of the well-known non-human adenovirus, including those isolated from cattle, sheep, pigs and other mammalian species, or isolated from chickens, turkeys and other avian species (Wigand et al, supra).

Adenovirus inverted terminal repeats are about 100–150 bp in length. The length and sequence of the inverted terminal repeats varies with the serotype.

The DNA sequence of the inverted terminal repeats of Ad5 is shown in FIG. 1 (SEQ ID NO:1). It begins at nucleotide 1 and it ends at nucleotide 103.

The DNA sequences of inverted terminal repeats of other adenovirus serotypes, e.g., Ad2, Ad4, Ad5, Ad7, Ad9, Ad12, Ad18, and Ad31, are also well-known in the art (Tamanoi et al, supra).

For those adenovirus serotypes where the DNA sequence of the inverted terminal repeat has not yet been determined, the DNA sequence of the inverted terminal repeat can be readily determined by DNA sequencing (Sambrook et al, In: *Molecular Cloning. A Laboratory Manual*, Cold Spring Harbor Laboratory Press (1989)).

The adenovirus inverted terminal repeat for use in the present invention can be obtained by DNA cloning from adenovirus DNA or chemically synthesized (Sambrook et al, supra).

The packaging signal is required to encapsidate the viral DNA during the late phase of infection into the preformed capsids.

The particular adenovirus serotype employed in the present invention from which the packaging signal is derived or based upon which DNA sequence of the packaging signal is synthesized, is not critical. Examples of such adenovirus serotypes which can be employed in the present invention include those exemplified above.

The adenovirus packaging signal is about 100 bp in length. The length and sequence of the packaging signal varies with the serotype.

The DNA sequence of the packaging signal of Ad5 is shown in FIG. 1 (SEQ ID NO:1). The packaging signal begins at nucleotide 241 and ends at nucleotide 347.

The DNA sequences of the packaging signals of other adenovirus serotypes, e.g., Ad3 (Kosturko et al, *J. Virol.*, 43:1132–1137 (1982), Ad16 (Hammarskjold et al, supra), Ad7 and Ad12 (Hearing et al, supra) are also well-known in the art.

The packaging signal in Ad2 or Ad5 consists of 5 short homologous DNA sequences that have the 8 bp consensus sequence (A/T)AN(A/T)TTTG (Grable et al, supra).

For those adenovirus serotypes where the DNA sequence of the packaging signal has not yet been determined, the DNA sequence of the packaging signal can be readily determined by DNA sequencing (Sambrook et al, supra)

The adenovirus packaging signal for use in the present invention can be obtained by DNA cloning from adenovirus DNA or chemically synthesized (Sambrook et al, supra).

As used herein, the expression "foreign gene" means any gene which encodes a foreign protein or RNA.

The foreign gene encoded and expressed by the adenovirus vectors of the present invention is not critical. By definition herein, the foreign gene is foreign to adenoviruses, but is not necessarily foreign to the target cell type which is infected by the recombinant adenovirus of the present invention.

As used herein, the expression "foreign protein" means any protein which is not expressed by wild-type adenovirus.

The particular foreign protein which can be employed in the present invention is not critical thereto. The protein can be, e.g., a muscle protein, a coagulation protein, a membrane protein, a urea cycle protein or a serine protease.

Specific examples of such foreign proteins which can be employed in the present invention include dystrophin (Hoffman et al, *Cell*, 51:919 (1987)), coagulation factor VIII (Wion et al, *Nature*, 317:726 (1985)), Cystic Fibrosis Transmembrane Regulator Protein (CFTR) (Anderson et al, *Science*, 251:679 (1991); and Crawford et al, *Proc. Natl. Acad. Sci., USA*, 88:9262 (1991)), Ornithine Transcarbamylase (OTC) (Murakami et al, *J. Biol. Chem.*, 263:18437 (1988)), α1-antitrypsin (Fagerhol et al, In: *Hum. Genet.*, Vol. 11, Harris Ed., Plenum, N.Y., p. 1 (1981)).

The genes encoding many foreign proteins are well-known in the art, and can be cloned from genomic or cDNA libraries (Sambrook et al, supra). Examples of such genes include the dystrophin gene (Lee et al, *Nature*, 349:334 (1991)), the Factor VIII gene (Toole et al, *Nature*, 312:342 (1984)), the CFTR gene (Rommens et al, *Science*, 245:1059 (1989); and Riordan et al, *Science*, 245:1066 (1989)), the OTC gene (Horwich et al, *Science*, 224:1068 (1984)), and the α1-antitrypsin gene (Lemarchand et al, *Proc. Natl. Acad. Sci., USA*, 89:6482 (1992)).

In addition, genes encoding foreign proteins such as Rb, for the treatment of vascular proliferative disorders like atherosclerosis (Chang et al, *Science*, 267:518 (1995)), and p53 for the treatment of cancer (Wills et al, *Hum. Gene Ther.*, 5:1079 (1994); Clayman et al, *Canc. Res.*, 55:1 (1995)), and HIV disease (Bridges et al, *Lancet*, 345:427 (1995)), can be employed in the present invention.

The gene transfer vector does not need to code for a functional gene product, i.e., it may also code for a partial gene product which acts as an inhibitor of a eukaryotic enzyme (Warne et al, *Nature*, 364:352–355 (1993); and Wang, *J. Cell Biochem.*, 45:49–53 (1991)).

The particular foreign RNA which can be employed in the present invention is not critical thereto. Examples of such RNAs include anti-sense RNA (Magrath, *Ann. Oncol.*, 5(Suppl 1):67–70 (1994); Milligan et al, *Ann. NY Acad. Sci.*, 716:228–241 (1994); and Schreier, *Pharma. Acta Helv.*, 68:145–159 (1994)), and catalytic RNA (Cech, *Biochem. Soc. Trans.*, 21:229–234 (1993); Cech, *Gene*, 135:33–36 (1993); Long et al, *FASE J.*, 7:25–30; and Rosi et al, *Pharm. Therap.*, 50:245–254 (1991)).

The vector of the present invention may additionally comprise a gene encoding a marker or reporter molecule to more easily trace expression of the vector.

The particular marker gene which can be employed in the present invention is not critical thereto. Examples of such marker genes which can be employed in the present invention are well-known in the art and include β-galactosidase (Fowler et al, *Proc. Natl. Acad. Sci., USA*, 74:1507 (1977)), luciferase (Tu et al, *Biochem.*, 14:1970 (1975)), and chloramphenicol acetyltransferase (Gorman et al, *Mol. Cell Biol.*, 2:1044–1051 (1982)).

The vector may contain more than one gene encoding the same or different foreign proteins or RNAs. The maximum number of genes which can be present in the vector will vary depending upon the size of the individual foreign genes. Generally speaking, the total amount of DNA in the vector can be about 38 kb. Typically, the vector will contain up to 37 kb, preferably up to approximately 32 kb of DNA encoding foreign protein(s) or RNA(s). Preferably the size of the vector is smaller than the size of the adenovirus genomic DNA.

The vector may be a circular plasmid, wherein the said first adenovirus inverted terminal repeat is ligated head to head to said second adenovirus inverted terminal repeat. This can be achieved by either ligating the inverted terminal repeats head to head after isolation from adenovirus DNA or after subcloning of the inverted terminal repeats into plasmids using T4 DNA ligase (Sambrook et al, supra), or by isolating head to head ligated inverted terminal repeats from infected cells as described by Graham, *EMBO J.*, 3:2917 (1984). In this embodiment, it is preferably that a unique restriction site is present between said first adenovirus inverted terminal repeat and said second adenovirus inverted terminal repeat. Unique means that only a single cleavage site of a particular recognition sequence is present in the plasmid.

The particular unique restriction site which can be employed in the present invention is not critical thereto. Examples of such unique restriction sites which can be employed in the present invention are well-known in the art and include PmeI and NotI. The restriction enzymes are commercially available, e.g., from New England Biolabs (Beverly, Mass.) or Boehringer Mannheim (Mannheim, Germany). The choice of the introduced unique restriction site varies depending on the sequence of the plasmid. Usually the introduced restriction site corresponds to a DNA sequence recognized by a rare cutting restriction enzyme.

The particular unique restriction site can be introduced between the inverted terminal repeats by DNA cloning using T4 DNA ligase (Sambrook et al, supra).

Alternatively, the vector may be a linearized plasmid. The plasmid may be linearized, e.g., by enzymatically cleaving at a unique restriction site. The inverted terminal repeats, one or both of which contains a packaging signal, may be ligated to both ends of the linearized plasmid DNA using T4 DNA ligase.

The inverted terminal repeats may be either obtained directly from adenovirus DNA with or without the terminal protein attached thereto, or they may be obtained by isolation from a plasmid after subcloning of the inverted terminal repeats into plasmids (Sambrook et al, supra).

The vector of the present invention may be synthesized by DNA ligation of different DNA fragments (Sambrook et al, supra).

In another embodiment, the above-described objects of the present invention have been met by recombinant adenovirus virus particles which have encapsidated therein the gene transfer vector. The recombinant adenovirus particles are produced by the process comprising the steps of:

(1) co-transfecting adenovirus host cells with
  (A) adenovirus genomic DNA, and
  (B) the gene transfer vector;
(2) harvesting adenovirus particles produced by the resulting host cells; and
(3) separating, by CsCl centrifugation, adenovirus particles which have encapsidated therein said adenovirus genomic DNA from recombinant adenovirus particles which have encapsidated therein said gene transfer vector.

As used herein, the expression "recombinant adenovirus particle" means particles having an adenovirus capsid, and which contain therein the gene transfer vector instead of adenovirus genomic DNA.

As used herein, the expression "adenovirus genomic DNA" means DNA that contains all or most of the information to produce adenovirus particles. Typically, this information includes the genes that encode adenovirus functions, e.g., adenovirus DNA polymerase, penton protein, hexon protein and other viral proteins or RNA,. These function are well-known in the art (*Adenovirus DNA*, Doerfler, Ed., Martinus Nijhoff Publishing, Boston (1986)). When the DNA does not contain all of the information to produce adenovirus particles, the missing information is supplied by the adenovirus host cells.

The particular adenovirus serotype from which the adenovirus genomic DNA employed in the present invention is derived is not critical thereto. Examples of such adenovirus serotypes include those discussed above.

In a preferred embodiment, the adenovirus genomic DNA has an E1A$^-$ phenotype. More preferably, the adenovirus genomic DNA has both an E1A$^-$ phenotype and an E1B$^-$ phenotype. Most preferably, the adenovirus genomic DNA has an E1A$^-$, E1B$^-$, and E4$^-$ phenotype. Also mutations in other adenovirus functions, e.g., E2A and E3 can be present.

The E1A$^-$ phenotype is preferably the result of a deletion in the E1A region. Similarly, E1B$^-$, E2A$^-$ and E4$^-$ phenotypes are preferably the result of a deletion in the E1B, E2A and E4 regions, respectively. Adenovirus mutants containing such deletions are well-known in the art and include:

E1A$^-$: H5dl1311and H5dl1312 (Jones et al, *Cell*, 13:181–188 (1978); Jones et al, *Cell*, 17:683–689 (1979); and Jones et al, *Proc. Natl. Acad. Sci., USA*, 76:3665–3669 (1979)).

E1B$^-$: H5dl313: (Jones et al, *Cell* 17:683–689 (1979).

E2A$^-$: Zhou et al, supra.

E4$^-$: Perricaudet et al, supra; and Fines et al, supra.

It is also preferable that the adenovirus genomic DNA has a defective packaging signal so as to give the recombinant adenovirus a packaging, and thus a growth, advantage. In this way, simple serial propagation will increase the titer of the recombinant adenovirus with each passage on adenovirus host cells. Further, by using a packaging impaired genomic DNA it is possible to avoid, upon CsCl centrifugation, the enrichment of adenovirus mutant particles that have deletions in the right part of the viral genome, as such particles may have densities comparable to recombinant adenovirus particles having encapsidated therein the gene transfer vector.

The defective packaging signal is preferably the result of a deletion in the packaging signal. Adenovirus mutants containing such deletions are well-known in the art and include dl309-336/358, dl309-317/358, dl309-293/358, dl309-287/358, dl309-274/358 and dl309-267/358 (Grable et al, supra), as well as SV5 prepared in Example 3 below.

Defective packaging can also induced by enlarging the size of the adenovirus genomic DNA up to a size that the overall packaging efficiency is impaired. That is, the maximum size of viral DNA to be packaged in viral capsids is about 38 kb. Larger DNAs are not, or only very inefficiently, packaged into adenovirus particles. By increasing the size of the adenovirus genomic DNA up to or beyond 38 kb, and keeping the size of the gene transfer vector smaller, it is possible to select for packaging of the gene transfer vector into the adenovirus particles.

The adenovirus genomic DNA that is used for co-transfection can be either:

(a) purified adenovirus DNA, which as been, for example, obtained from adenovirus particles after CsCl centrifugation thereof, as described by Mitani et al, *Proc. Natl. Acad. Sci., USA*, 92:3854 (1995);

(b) adenovirus DNA, which has been prepared in a way that the terminal protein is still attached to the viral terminus, and has been purified, for example, by gel filtration or sucrose gradient centrifugation, as described by Chinnadurai et al, *J. Virol.*, 26:195–199 (1978); or (c) adenovirus DNA, which has been freed from the virion capsid as in (b) with the terminal protein still attached to the terminus, but that has not been purified by gel filtration or sucrose centrifugation, rather such is directly used for transfection after lysing the adenovirus particles by incubation on ice for 20 min in a buffer comprising 8.0 M guanidinium hydrochloride, 10 mM Tris-HCl (pH 7.5), 2.0 mM EDTA and 4.0 mM β-mercaptoethanol.

Method (c) is preferable, as such yields the most reliable results, and is the most efficient.

The particular adenovirus host cells which can be employed in the present invention are not critical thereto. Examples of such adenovirus host cells which can be employed in the present invention are well-known in the art and include human 293 cells (a human embryonic kidney cell line that constitutively produces E1 proteins) (Graham et al, *Virol.*, 52:456 (1973)). Currently this is the only available cell line providing the E1 function. Other examples of adenovirus host cells include HeLa (ATCC CCL 2) and the KB cell line (ATTC CCL 17).

It is required when using adenovirus genomic DNA which has an E1A$^-$ phenotype, that in the adenovirus host cells adenovirus, E1 proteins are expressed. This is because the E1 function is required for viral propagation. Human 293 cells are an example of such adenovirus E1A$^+$ host cells.

Co-transfection of adenovirus host cells can be carried out by well-known methods, such as the calcium phosphate transfection procedure, as described by Graham et al, *Virol.*, 52:456–467 (1973), or using lipofectamine (Gibco BRL, Gaithersburg, Md.).

The ratio of adenovirus genomic DNA to gene transfer vector employed in the co-transfection step is not critical to the present invention, and may vary depending upon the method used for transfection. Generally, the weight ratio will be about 1 to 100, preferably about 1 to 50.

Harvesting of the adenovirus particles produced by the co-transfected host cells can be carried out by well-known methods, such as resuspension of the cells in phosphate buffered saline (PBS) containing 5–10% (v/v) glycerol, followed by preparation of a cell extract by freezing and thawing of the cells, as described by Mitani et al, supra.

After co-transfection of the adenovirus host cells, the cell monolayer is generally either:

(a) overlayed with 0.5% (w/v) agarose containing medium for about 3 to 10 days until individual viral plaques appear representing infected cells. Individual plaque isolates are then analyzed for the presence of the foreign DNA having the inverted terminal repeats with the packaging signal within viral particles, for example, by the polymerase chain (PCR) reaction using forward and reverse primers homologous to the foreign gene present in the gene transfer vector; or (b) not overlayed with agarose. After the cell monolayer is completely lysed, the virus is harvested, and analyzed for the presence of the foreign DNA in virus particles, e.g., by PCR.

Method (a) is preferable because by directly isolating individual plaque isolates it is easier to propagate a uniform and clonal recombinant adenovirus isolate.

If the gene transfer vector contains a marker gene, e.g., β-galactosidase, it is also possible to stain the monolayer by adding an additional overlay containing substrate for the protein encoding by the marker gene, e.g., 0.01% (w/v) 5-bromo-4-chloro-3-indolyl β-D-galactoside (X-gal).

Both methods (a) and (b) lead to a mixed virus population consisting of (i) the recombinant adenovirus particles and (ii) adenovirus particles containing adenovirus genomic DNA. All of the protein functions which are necessary for the replication and packaging of the foreign DNA into virus particles, as well as all other viral proteins, like the capsid proteins, are encoded by the adenovirus genomic DNA in this system.

After this step, the mixed virus population is serially passaged, e.g., about 4–8 times, in adenovirus host cells in order to increase the number of recombinant virus particles.

The adenovirus particles which have encapsidated therein the adenovirus genomic DNA can be separated from recombinant adenovirus particles which have encapsidated therein the gene transfer vector by CsCl centrifugation. For example, after serial passage on adenovirus host cells, the infected cells are collected by centrifugation in a cell centrifuge (Beckmann) at 400×g, and then the cells are resuspended in PBS containing 5–10% (v/v) glycerol. A cell extract is prepared by freezing the resuspended cells three times in liquid nitrogen, or alternatively, in a ethanol/dry ice bath, and thawing at 37° C. After spinning down the cell debris at 1000×g, the resulting cell extract is subjected to equilibrium centrifugation in a 50% (w/v) CsCl gradient. For every 1.0 ml of cell extract, 0.5 g of CsCl is dissolved therein. A total volume of 10 ml can be subjected to ultracentrifugation in SW41 ultracentrifugation tubes (Beckmann) in a SW41 rotor (Beckmann) at 32,000 rpm (175,587×g at $r_{max}$) for more than 16 hr at 4° C.

It was surprisingly found in the present invention, that upon CsCl centrifugation, the recombinant adenovirus particles can be well separated from the adenovirus particles containing adenovirus genomic DNA based on a difference in buoyant densities of the two types of particles.

It is not clear why there is a difference in buoyant density between the two types of particles leading to 2 distinct bands in the CsCl gradient. It is unlikely that this is due to a difference in the size of the DNA's itself. Rather, it is believed that the observed difference in buoyant densities might be due to a difference in the number of DNA-associated proteins within the viral capsid.

Electron microscopic examination indicates that the adenovirus particles and the recombinant adenovirus particles have the same size, and are morphologically indistinguishable.

The upper band in the CsCl gradient containing the recombinant adenovirus particles is isolated, and can be subjected to 1 or 2 additional CsCl centrifugation steps in order to increase the purity of the recombinant adenovirus particles. The upper band contains at least 100-fold more infectious recombinant adenovirus particles than infectious adenovirus particles containing adenovirus genomic DNA. Because, in a preferred embodiment, the adenovirus particles containing adenovirus genomic DNA is E1A$^-$ and, therefore, cannot replicate in normal human cells, this level of purity is believed to be acceptable for in vivo gene therapy. The titer of the recombinant adenovirus particles can be further increased by co-infection of adenovirus host cells with a higher ratio of the recombinant adenovirus particles, obtained after CsCl purification, to adenovirus particles.

After CsCl centrifugation, the recombinant adenovirus particles can be dialyzed against PBS or Tris-buffered saline to remove the CsCl, and stored at −20 to −80° C. prior to use.

Alternatively, the recombinant adenovirus particles of the present invention can be lyophilized, and then stored prior to use at −20 to −80° C. The recombinant adenovirus particles can then be reconstituted with water or a physiological solution or medium prior to use.

With the currently available vectors, it is believed that expression of viral proteins within the infected cells stimulates a cellular immune response of the host against the infected cells, resulting in only transient expression of the foreign gene. However, in the present invention, all of the viral genes encoding adenovirus proteins are preferably substituted by the foreign DNA in the recombinant adenovirus particles. Thus, it is expected that the immunogenicity of the recombinant adenovirus particles is considerably reduced or abolished, and the problem of transient expression of the foreign gene can be overcome.

In yet still another embodiment, the above-described objects of the present invention have been met by a method for introducing and expressing a foreign gene in eukaryotic cells comprising infecting said eukaryotic cells with the above recombinant adenovirus particles which have encapsidated therein the gene transfer vector.

The multiplicity of infection is not critical to the present invention. Generally the multiplicity of infection will be in the range of about 1 to 100, preferably in the range of about 1 to 10.

Infection can be carried out in vitro or in vivo. In vitro infection of cells is performed by adding recombinant adenovirus particles to the cell culture medium. When infection is carried out in vivo, the solution containing the recombinant adenovirus particles may be administered by a variety of modes, depending on the tissue which is to be infected. Examples of such modes of administration include injection of recombinant adenovirus particles into the arterial or venous vascular system, injection of recombinant adenovirus particles directly into a tissue (e.g., liver, brain or muscle), direct application to a surface (e.g., skin or bladder), or instillation into an organ (e.g., lung or gastrointestinal tract).

The particular eukaryotic cell to be infected in the present invention is not critical. Examples of such eukaryotic cells include liver cells, muscle cells, lung cells, and tumor cells. The cells may be derived from any animal, e.g., mammals, such as humans, as well as avian species.

The capacity of the gene transfer vector for DNA is large. Thus, other elements can be included in the gene transfer element, e.g., promoters, cell specific enhancer sequences, a hormone responsive element, mammalian artificial chromosome elements or elements from the autonomous replicating circular minichromosomes, or elements that can be regulated by chemical substances.

The particular tissue specific promoters employed is not critical to the present invention.

Viral or mammalian promoters are suitable to achieve expression of the foreign protein. For example, the SV40 promoter and the cytomegalovirus promoter (Andersson et al, *J. Biol. Chem.*, 264:8222–8229 (1989)) will result in a constitutive high-level expression of the foreign protein in the infected cells; and the human t-PA gene promotor (Fisher et al, *J. Biol. Chem.*, 260:11223–11230 (1985)) will result in expression of the foreign protein in a well-known regulated manner. By employing a promotor with well-known properties, the pattern of expression of the foreign protein following infection of a target cell population can be optimized.

Selection of a promotor which is active in only a specific cell-type will enhance tissue-specific expression of a foreign gene. For example, use of the MCK promoter will lead to expression in skeletal and cardiac muscle, but not in liver tissue. Additional examples of tissue specific promoters include, but are not limited to, α S1- and β-casein promoters which are specific for mammary tissue (Platenburg et al, *Trans. Res.*, 3:99–108 (1994); and Maga et al, *Trans. Res.*, 3:36–42 (1994)); the phosphoenolpyruvate carboxykinase promoter which is active in liver, kidney, adipose, jejunum and mammary tissue (McGrane et al, *J. Reprod. Fert.*, 41:17–23 (1990)); the tyrosinase promoter which is active in lung and spleen cells, but not testes, brain, heart, liver or kidney (Vile et al, *Canc. Res.*, 54:6228–6234 (1994)); the involucerin promoter which is only active in differentiating keratinocytes of the squamous epithelia (Carroll et al, *J. Cell Sci.*, 103:925–930 (1992)); and the uteroglobin promoter which is active in lung and endometrium (Helftenbein et al, *Annal. N.Y. Acad. Sci.*, 622:69–79 (1991)).

Alternatively, cell specific enhancer sequences can be used to control expression, for example human neurotropic papovirus JCV enhancer regulates viral transcription in glial cells alone (Remenick et al, *J. Virol.*, 65:5641–5646 (1991)). Yet another way to control tissue specific expression is to use a hormone responsive element (HRE) to specify which cell lineages a promoter will be active in, e.g., the MMTV promoter requires the binding of a hormone receptor, such as progesterone receptor, to an upstream HRE before it is activated (Beato, *FASEB J.*, 5:2044–2051 (1991); and Truss et al, *J. Steroid Biochem. Mol. Biol.*, 41:241–248 (1992)).

Additional genetic elements may be included on the gene transfer vector in order to modify its behavior inside the recipient animal cell (Hodgson, *Bio/Technology*, 13:222–225 (1995)). Such elements include, but are not limited to, mammalian artificial chromosome elements or elements from the autonomous replicating circular minichromosomes, such as found in DiFi colorectal cancer cells, to allow stable non-integrated retention of the expression cassette (Huxley et al, *Bio/Technology*, 12:586–590 (1994); and Untawale et al, *Canc. Res.*, 53:1630–1636 (1993)), intergrase to direct integration of the expression cassette into the recipient cells chromosome (Bushman, *Proc. Natl. Acad. Sci.*, USA, 91:9233–9237 (1994), the inverted repeats from adeno-associated virus to promote non-homologous integration into the recipient cells chromosome (Goodman et al, *Blood*, 84:1492–1500 (1994), recA or a restriction enzyme to promote homologous recombination (PCT Patent Publication No. WO9322443 (1993); and PCT Patent Publication No. WO9323534-A (1993)), elements that direct nuclear targeting of the eukaryotic expression cassette (Hodgson, supra; and Lewin, *Genes V*, Oxford University Press, Oxford (1994)), or elements that can be regulated by chemical substances, e.g., tetracycline responsive elements that can mediate reversible transcriptional activation or repression of gene activity upon administration or withdrawal of tetracycline (Furth, *Proc. Natl. Acad. Sci.*, USA, 91:9302–9306 (1992))

In a further embodiment, the above-described objects of the present invention have been met by a method for treatment of muscular dystrophy comprising infecting muscle cells with recombinant adenovirus particles of the present invention which have encapsidated therein a gene transfer vector encoding the dystrophin gene.

The muscle cells can be infected with the recombinant adenovirus particles in the same manner, and in the same amounts as discussed above for other eukaryotic cells.

The following examples are provided for illustrative purposes only, and are in no way intended to limit the scope of the present invention.

EXAMPLE 1

Preparation of Gene Transfer Vector pKM74

Figure 3B:
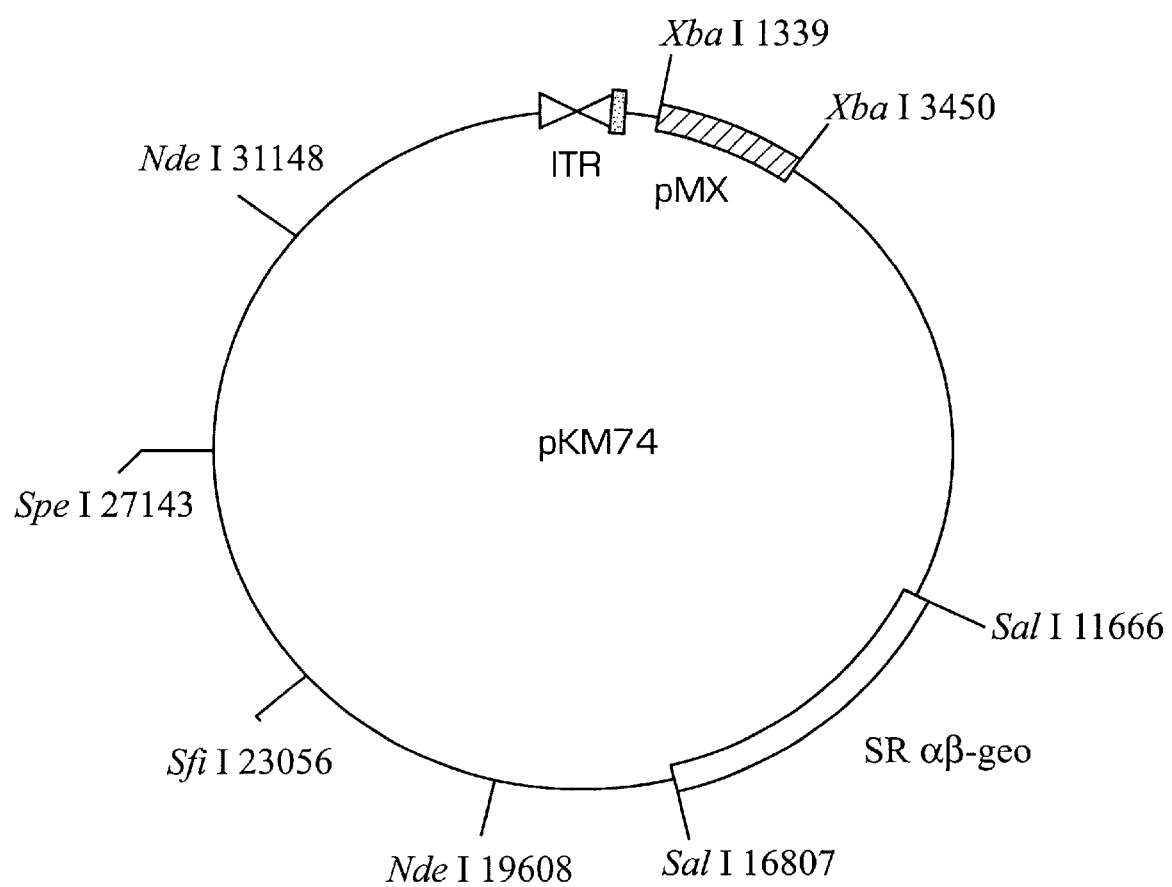

Plasmid pKM74 is a derivative of pFG140 (FIG. 3A). pFG140 is an infectious circular Ad5 genomic DNA which has an insertion of pMX2, a 2.2 kb derivative of pBR322 containing a plasmid replication origin and the ampicillin resistance gene, at the XbaI site in the E1A region of Ad5 (Graham, *EMBO J.*, 3:2917–2922 (1984)). After transfection into human 293 cells, pFG140 is replicated and packaged as linear molecules into viral particles to produce E1⁻ Ad5.

pKM74 was obtained by replacing the 6.9 kb and 0.4 kb SalI fragments, between map units 26.3 and 46.6, in pFG140 (corresponding to nucleotides 9466 to 16750) with a SRαβ-geo expression cassette, resulting in a plasmid of approximately 36 kb in length, which is approximately the same as that of a wild-type Ad5 (FIGS. 3A and 3B).

More specifically, 3.0 μg of pβ-geo (Friedrich et al, *Genes & Dev.*, 5:1513–1523 (1991)), a plasmid containing a bifunctional fusion gene of the *E. coli* β-galactosidase (β-gal) gene and the neomycin resistance gene (neo), was digested with SalI and XhoI. The resulting digested DNA was subjected to 0.7% (w/v) agarose gel electrophoresis, and 0.6 μg of the resulting 3.9 kb DNA fragment containing the β-geo gene was purified using the glass matrix method (Prep-A-Gene Kit, BIORAD, Hercules, Calif.).

5.0 μg of pCDLSRα296 (Takebe et al, *Mol. Cell. Biol.*, 8:466–472 (1988)) was then digested with XhoI, dephosphorylated with calf intestinal alkaline phosphatase (CIAP) (Pharmacia). The resulting digested DNA was subjected to 0.8% (w/v) agarose gel electrophoresis, and 1.0 μg of a DNA fragment containing the SRα promoter was recovered.

Next, 30 ng of the DNA fragment containing the β-geo gene was ligated to 25 ng of the DNA fragment containing the SRα promoter using a DNA ligation kit (Takara, Kyoto, Japan). In this manner, the β-geo fragment was subcloned between the XhoI sites of pCDLSRα296, thereby removing the splicing signal and a stuffer from pCDLSRα296, and giving rise to pSRαβ-geo.

3.0 μg of pSRαβ-geo was digested with SalI, and dephosphorylated, as described above. The resulting digested DNA was subjected to 0.8% (w/v) agarose gel electrophoresis, and 1.6 μg of the resulting SRαβ-geo cassette (5.0 kb) was recovered.

80 ng of the SRαβ-geo cassette was ligated to 20 ng of SalI-digested pFG140 using T4 DNA ligase, to give rise to pKM74.

In pKM74, the coding regions of LI (encoding penton-associated protein), L2 (encoding core proteins), VAI and VAII, pTP, as well as the third late leader, were partially or completely deleted, totaling about 7.2 kb (FIG. 3A). Therefore, transfection of pKM74 into human 293 cells does not produce any progeny virus, although some of the viral proteins are still expressed.

pKM74, like the infectious plasmid pFG140, has the Ad5 packaging signal, which is located at the 5' end of the genome, between nucleotides 194–358, and two inverted terminal repeats (nucleotides 1–103) covalently joined, which act as an origin of replication (FIGS. 3A and 3B). It was postulated in the present invention that the origins of replication in the inverted terminal repeats should allow this plasmid to be replicated in cells co-transfected with Ad2 genomic DNA, as a result of expression of the Ad2 proteins, including the viral DNA polymerase, the DNA binding protein and pTP, from the Ad2 genomic DNA (Hay et al, *J. Mol. Biol.*, 175:493–510 (1984)). Further, it was postulated in the present invention that following replication as a viral genome, the plasmid DNA, as well as the Ad2 genomic DNA, would be encapsidated as linear molecules in adenovirus particles.

As discussed above, pKM74 itself is replication-incompetent. Thus, this system is similar to that of retroviral vectors (Miller, In: *Current Topics in Microbiology and Immunology*, Springer-Verlag, Berlin, Vol. 158, pp. 1–24 (1992)), and herpes simplex virus type 1 (HSV-1) amplicon vectors (Breakefield et al, *The New Biologist*, 3:203–218 (1991)).

EXAMPLE 2

Production of Recombinant Adenovirus KM74

5.0 μg of pKM74 were co-transfected with 100 ng of wild-type Ad2 (ATCC No. VR-846) genomic DNA into monolayers of human 293 cells (Graham et al, *J. Gen. Virol.*, 36:59–74 (1977)), a human embryonic kidney cell line that constitutively produces E1 proteins, by the calcium phosphate transfection procedure (Graham et al, supra).

The 293 cell line was maintained in Minimum Essential Medium (MEM) supplemented with heat-inactivated 10% (v/v) newborn calf serum and 2.0 mM L-glutamine.

The Ad2 genomic DNA was purified as a complex with the terminal protein using a Sepharose CL-4B column, dialyzed against buffer comprising 10 mM Tris-HCl (pH 7.5), 1.0 mM EDTA and 2.0 mM β-mercaptoethanol, as described by Chinnadurai et al, *J. Virol.*, 26:195–199 (1978), and stored at 4° C.

More specifically, after CsCl purification and dialysis of Ad2 against PBS containing 10 mM $CaCl_2$ and 10 mM $MgCl_2$ (hereinafter "PBS$^{2+}$"), Ad2 DNA, with the terminal proteins still attached to the termini, was freed from the viral capsid by incubation with an equal volume of buffer comprising 8.0 M guanidine hydrochloride, 20 mM Tris-HCl (pH 7.5), 2.0 mM EDTA and 4.0 mM β-mercaptoethanol, at 4° C. for 20 min. The resulting extract was subjected to gel filtration using a sepharose CL-4B column (Pharmacia Biotech Inc, Piscataway, N.J.), which had been pre-equilibrated with buffer comprising 4.0 M guanidine hydrochloride, 10 mM Tris, 1.0 mM EDTA and 2.0 mM β-mercaptoethanol, and about 500 μl fractions were collected using a fraction collector (Pharmacia Biotech Inc). The optical density of the individual fractions was measured at a wavelength of 260 nm using an UV-Spectrophotometer (Beckmann) to determine which fractions contained the Ad2 DNA. Those fractions containing Ad2 DNA were dialyzed as dicussed above, used for transfection with pKM74, as discussed above.

The resulting transfected monolayers were overlayed with 0.5% (w/v) agarose-containing medium (Graham et al, In: *Gene Transfer and Expression Protocols*, Eds. Murray, Humana Press, Clifton, N.J., Vol. 7, pp. 109–128 (1991)). After plaques became visible, an additional overlay of agarose containing medium containing 0.01% (w/v) X-gal was added to detect plaques expressing β-gal as a result of the SRαβ-geo cassette in pKM74.

About 1–5% of the plaques turned blue, suggesting that pKM74 was packaged and propagated as virus in these plaques. The blue plaques were picked, and suspended in 500 μl of PBS$^{2+}$ containing 10% (v/v) glycerol.

The titer of the SRαβ-geo-containing recombinant virus, designated "KM74 virus", was determined by infecting the COS-7 monkey kidney cell line (ATCC No. CRL-1651), followed by X-gal staining 16 hr later, as described by MacGregor et al, In: *Gene Transfer and Expression Protocols*, Eds. Murray, Humana Press, Clifton, N.J., Vol. 7, pp. 217–235 (1991).

More specifically, confluent COS-7 cells monolayers were infected by adding freeze/thaw cell extract from the plaques to the medium. 16 hr later, the cells were fixed with 0.5% (v/v) glutaraldehyde (Sigma, St. Louis, Mo.) in PBS, and stained with X-gal as described by MacGregor et al, supra.

The COS-7 cells were maintained in Dulbecco's modified Minimum Essential Medium (DMEM) supplemented with heat-inactivated 10% (v/v) newborn calf serum.

A variable number of blue cells (0–400) was observed in different wells after infection with 50% of the virus suspension. No blue cells were observed when virus was heat-inactivated at 60° C. for 30 min, suggesting that the expression of β-gal was not caused by contaminating parental pKM74 DNA.

Blue-plaque isolates #9 and #12, which yielded the highest number of blue cells on COS-7 cells, were expanded by successive propagation on human 293 cells in 24 well, 60 mm and 150 mm dishes. That is, the recombinant KM74 virus itself is defective. Thus, for propagation, it needs the presence of Ad2 in the same cell to provide all required viral functions. Hence, serial propagation was performed such that upon infection of adenovirus host cells, complete cytopathic effect (CPE) was observed 48 hr post-infection. This corresponds to an infection with about 5 to 10 m.o.i. of Ad2 virus.

More specifically, for infection of 3.6×10$^4$ human 293 cells in 24 wells, 200 μl of the primary plaque isolate was used for infection. 48 hr after infection, when CPE was apparent by microscopic observation, i.e., all of the cells were rounded up and/or floating, the infected cells were collected and resuspended in 250 μl of PBS$^{2+}$ containing 10% (v/v) glycerol. A cellular extract was then prepared by 3 times freezing and thawing in an ethanol/dry ice bath and in a 37° C. water bath, respectively. The cellular debris was removed by centrifugation at 1000×g, and between 2.0 and 50 μl of the cell extract was used to infect 1.0×10$^6$ human 293 cells in 60 mm cell dishes. This sequence of infection of human 293 cells with cell extract, harvesting of the cells 48 hr post-infection and preparation of cell extract before new human 293 cells were infected, was repeated 4 times until enough virus was obtained to infect 4.0×10$^7$ human 293 cells in seven 150 mm dishes.

At each propagation step, an aliquot of the infected cell extract was used to infect COS-7 cells plated to confluency in 24 well dishes, and tested for X-gal staining, as described above. The appearance of blue-staining in increasing amounts after each propagation step indicated that the presence of increasing amounts of KM74 virus, and thus, that the KM74 virus was replicating.

To determine the appropriate amount of input virus that was needed to obtain good amplification of the KM74 virus at each step, different amounts of KM74 virus were used to infect one 60 mm dish of human 293 cells. After 48 hr, the cell pellet, obtained by centrifugation of the cells in a cell centrifuge (Beckman), was suspended in 1.0 ml of PBS$^{2+}$ containing 10% (v/v) glycerol. The titer of the recombinant KM74 virus was determined by infecting COS-7 cells with 10 μl of the extract obtained by 3 times freezing and thawing as described above, followed by X-gal staining, as described above. The results are shown in Table 1 below.

TABLE 1

| input virus (m.o.i) | X-gal-positive COS-7 cells | total yield | increase |
|---|---|---|---|
| 40 | 140 | 1.4 × 10$^4$ | ×350 |
| 100 | 100 | 1.0 × 10$^4$ | ×100 |
| 400 | 60 | 0.6 × 10$^4$ | ×15 |
| 1000 | 160 | 1.6 × 10$^4$ | ×16 |

As shown in Table 1 above, when the cells were infected at a very high m.o.i., the increase in KM74 virus titer was much smaller than that under optimal conditions. For example, 40 transducing KM74 particles of isolate #9 were amplified to 1.4×10$^4$ particles (350-fold increase) after one cycle of infection on one 60 mm dish, while 1000 transducing KM74 particles were amplified only to 1.6×10$^4$ particles (16-fold increase) on another 60 mm dish (see Table 1 above).

After propagation of KM74 virus isolates #9 and #12 in human 293 cells cultured in 150 mm dishes for 48 hr, the virus was extracted from the cell pellet by freezing and thawing, and then subjected to ultracentrifugation on a 50% (w/v) CsCl gradient at 175,587×g at $r_{max}$ for 18 hr at 4° C. The central part of the gradient, which contained a major band of the wild-type Ad2 particles, and also possibly recombinant KM74 virus particles, was fractionated by collection from the bottom of the centrifuge tube. Each fraction corresponded to one drop of about 50 μl. To analyze the distribution of the Ad2 particles in the gradient, DNA was extracted from the Ad2 particles in each fraction, and then subjected to slot blot hybridization with Ad2 DNA as a probe.

More specifically, 2.0 μl of each fraction was diluted in buffer comprising 10 mM Tris-HCl (pH 7.5) and 1.0 mM EDTA (hereinafter "TE buffer"), and incubated with 0.5 mg proteinase K per ml in TE buffer containing 0.5% (w/v) SDS at 55° C. for 16 hr. DNA was prepared by phenol/chloroform extraction, and ethanol precipitated (Sambrook et al, supra). The DNA was 0 then transferred to a nylon membrane (Gene Screen-Plus, DuPont NEN, Boston, Mass.) using a slot blot apparatus (Minifold II, Schleicher & Schuell, Inc., Keene, N.H.). The resulting membrane was hybridized with Ad2 DNA as a probe, as described by Sambrook et al, supra. After autoradiography, the intensity of the signal from each slot was quantified by using a laser densitometer (Ultroscan XL, Pharmacia Biotech Inc).

Figure 4A:
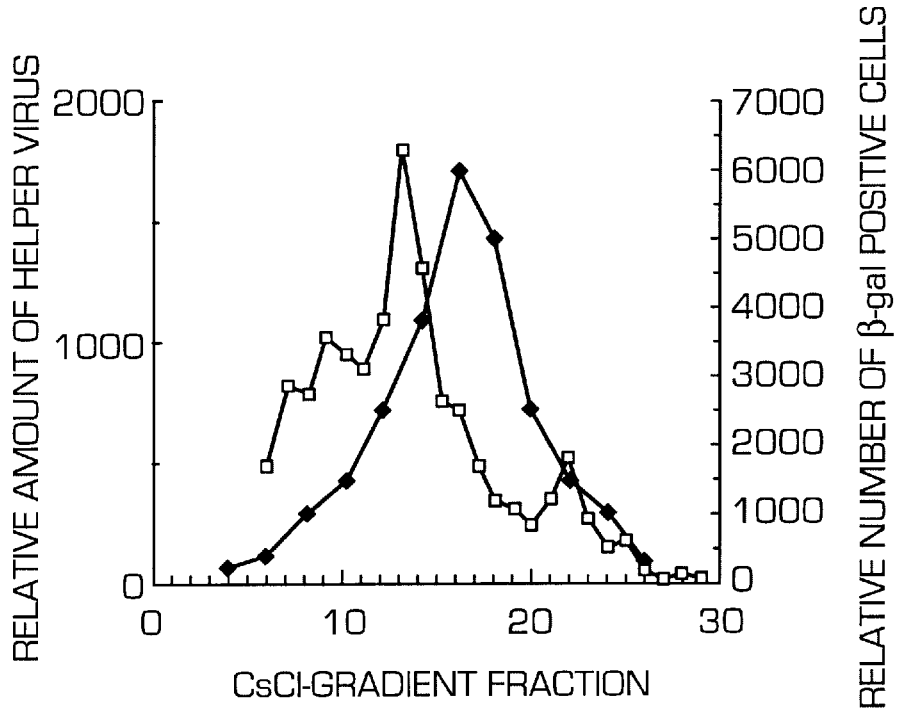
FIGS. 4A and 4B show analysis of the viral DNA in CsCl gradients for plaque isolates #9 (FIG. 4A) and #12 (FIG. 4B) obtained after co-transfection of human 293 cells with pKM74 and Ad2 genomic DNA. The copy number of Ad2 particles (□), and the number of KM74 particles (♦) are shown.
Figure 4B:
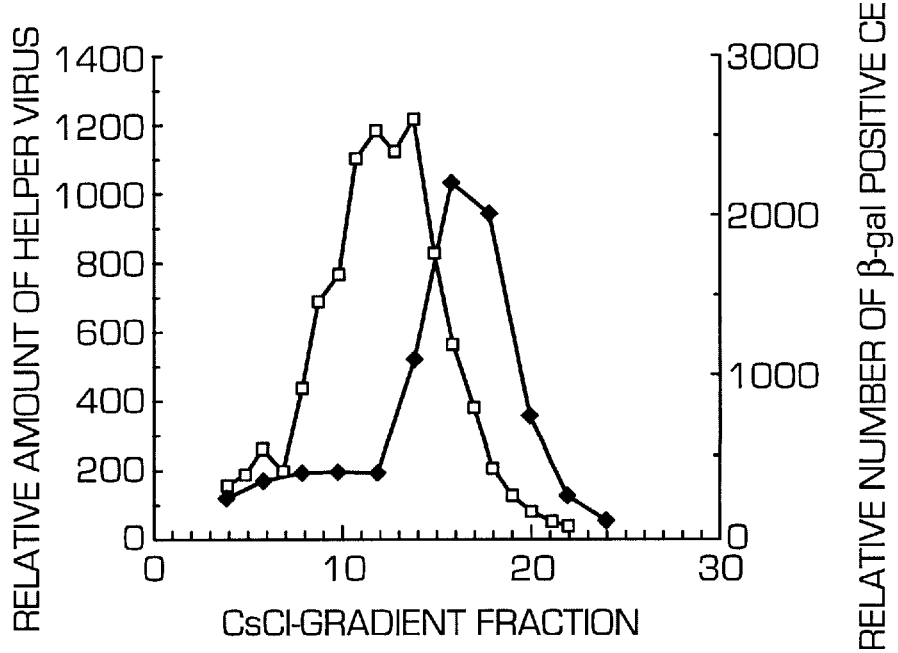

The relative intensity of the signal using Ad2 DNA as a probe, corresponding to the copy number of Ad2 virus particles (□), is shown in FIG. 4A (for isolate #9) and FIG. 4B (for isolate #12).

To measure the distribution of KM74 virus in the gradient, 0.5 μl of each fraction was used to infect COS-7 cells in 24 mm dishes, and analyzed for X-gal staining after 16 hr, as described above.

The number of blue cells after infecting COS-7 cells with each fraction, which corresponds to the number of KM74 virus particles (♦), is shown in FIG. 4A (for isolate #9) and FIG. 4B (for isolate #12).

In both isolates, the peak of Ad2 virus particles appeared between fraction 11 and 14, whereas the peak of KM74 virus particles appeared at a lower density (fraction 16 to 18). Therefore, it was possible to partially separate the recombinant KM74 virus particles from the wild-type Ad2 virus particles by an equilibrium density gradient centrifugation, even though the sizes of the genomes of the two viruses were similar, i.e., 37.8 kb for the FG140 virus and 35.7 kb for the KM74 virus.

The titer of the Ad2 virus particles at the peak (fraction 13) was about $2.0 \times 10^9$ plaque forming units/ml for both isolates. On the other hand, the titer of the recombinant KM74 virus particles at each peak was $4.4 \times 10^6$ transducing virus/ml (for isolate #9), and $1.2 \times 10^7$ transducing virus/ml (for isolate #12).

However, in view of the low sensitivity of the X-gal staining, which requires $10^3$ β-gal molecules to detect a signal (MacGregor, supra), the titer of the recombinant particles is likely to be underestimated.

DNaseI treatment of the KM74 virus particles did not abolish the β-gal activity, indicating that the recombinant genome, pKM74, was packaged into adenovirus particles.

To analyze the structure of the DNA in recombinant KM74 virus isolate #9, the three fractions from the CsCl centrifugation that showed the highest β-gal activity were pooled and dialyzed against TE buffer. Then, DNA was obtained from the pooled fractions, as described above, by incubating with 0.5 mg/ml proteinase K in TE buffer containing 0.5% (w/v) SDS at 55° C. for 16 hr, followed by phenol/chloroform extraction and ethanol precipitation. Next, a 2.0 μl aliquot of the resulting DNA, which had been resuspended in a total volume of 50 μl of TE buffer, was digested with HindIII, SacII, or XbaI, and the resulting digested DNA was subjected to 0.8% (w/v) agarose gel electrophoresis, and transferred to a nylon membrane (GeneScreen Plus, NEN) using a slot blot apparatus (MINIFOLD II, Schleicher & Schuell). The resulting DNA was subjected to Southern hybridization using 25 ng of SRαβ-geo DNA or 25 ng of pBR322 as a radioactively probe (Feinberg et al, *Anal. Biochem.*, 132:6 (1983); and Sambrook et al, supra). The restriction pattern of KM74 virus detected by the SRαβ-geo probe was identical to the expected pattern for the parental pKM74 plasmid. However, when the same blot was hybridized with the pBR322 probe, no signal was obtained, suggesting that the pMX2 sequence was deleted from the KM74 virus. The same result was obtained for KM74 virus isolate #12.

The deletion of the pMX2 sequence may have been the result of an early recombination event between Ad2 and pKM74 sequences in the left part of the viral genome. However, because of the lack of appropriate restriction sites distinguishing Ad2 and Ad5, it not possible to determine whether a recombination or deletion event had taken place in the KM74 virus. There is a high degree of homology between the pKM74 and Ad2 genomic DNA. Thus, in view of the high ratio of copy number, i.e., approximately 1000–2000:1, of Ad2 genomic DNA to that of the pKM74 employed, it would not be surprising if recombination occurred. It is also possible that a recombinant virus with the wild-type E1 sequence could have a growth advantage in human 293 cells over a recombinant virus without an intact E1 region. The deletion of the pMX2 sequence reduced the size of the recombinant virus genome. This reduction could explain why the recombinant KM74 virus particles appeared at a slightly lighter density than the wild-type Ad2 particles on the CsCl gradient.

EXAMPLE 3

Preparation of Adenovirus SV5

SV5 is an E1A⁻ E3⁻ Ad5 mutant containing a defective packaging signal, i.e., a 91 bp deletion within the left terminal packaging signal, thereby reducing the efficiency of packaging of SV5 genomic DNA into viral capsids (FIG. 2). SV5 was obtained as follows:

$1.5 \times 10^6$ human 293 cells were transfected with 5.0 μg of pFG140 (FIG. 3A) using the calcium phosphate transfection method as described by Graham et al, supra. From the resulting transfected cells, virus particles, designated as "FG140 virus", were plaque-purified as described by Graham et al, supra, and propagated in human 293 cells. Then, FG140 DNA was purified from the resulting propagated FG140 virus.

More specifically, after calcium phosphate transfection, the human 293 cell monolayer was overlayed with 10 ml of 0.5% (w/v) agarose containing medium. After 6 days, individual plaques were picked using pasteur pipettes, and then resuspended in 500 μl of PBS²⁺ containing 10% (v/v) glycerol. A larger amount of virus was prepared as described by (Graham et al, supra). The virus was dialyzed against TE buffer, followed by incubation in buffer comprising 50 mM Tris-HCl (pH 7.5), 20 mM EDTA and 0.5% (w/v) SDS, containing 0.5 mg proteinase K per ml. FG140 DNA was purified from the resulting solution by phenol/chloroform extraction and ethanol precipitation.

12 μg of the resulting pFG140 DNA was digested with XbaI, which cleaves at nucleotide 1339, and a 34.6 kb fragment of Ad5 DNA, extending from nucleotide 1339 to the right inverted terminal repeat, was isolated by 0.8% (w/v) agarose gel electrophoresis, and electroeluted using a Schleicher & Schuell electroelution apparatus.

In addition, the 389 bp left terminal fragment of Ad5 DNA was amplified by PCR using the packaging defective adenovirus mutant dl309-267/358 (Graeble et al, *J. Virol.*, 64:2047 (1990)) as the template. The forward primer used was: 5'-GGGCCCATCATCAATAATATACCTTATTTTG-3' (SEQ ID NO:3) which encompasses the left terminus, and includes an ApaI restriction site (bold); and the reverse primer used was: 5'-TGATCTAGACCGGGTATAAATACACTACACGTC-3' (SEQ ID NO:4) which extends from nucleotide 480 to nucleotide 457, and includes an XbaI restriction site (bold).

The PCR conditions used were: Denaturation at 94° C. for 5 min, followed by 35 cycles of denaturation (94° C. for 0.5 min), annealing (60° C. for 0.5 min) and extension (72° C. for 0.5 min), followed by a single extension step at 72° for 4 min.

dl309-267/358 has a deletion in three of the five elements constituting the packaging signal of Ad5, and is therefore packaging-impaired (FIG. 2). dl309-267/358 can be grown in cell culture only to an approximately 90-fold reduced titer compared to wild-type Ad5 (Graeble et al, supra).

The resulting amplified left terminal fragment was digested with XbaI, and then subcloned into the SmaI and XbaI sites of plasmid Bluescript II KS (Stratagene, La Jolla, Calif.). 30 μg of the resulting plasmid was then digested with EcoRI and XbaI, and subjected to 1.5% (w/v) agarose gel electrophoresis. The isolated left terminus was electroeluted, as described above, after visualization under UV light at a wavelength of 254 nm.

0.75 μg of the resulting purified left terminal fragment was dephosphorylated with calf intestinal phosphatase (CIP) according to the manufacturer's recommendation (New England Biolabs), and then ligated to 5.0 μg of the 34.6 kb XbaI fragment (nucleotide 1339 to the right inverted terminal repeat) of pFG140 DNA using T4 DNA ligase.

The ligation product was transfected into $1.5 \times 10^6$ human 293 cells in a 60 mm dish by the calcium phosphate transfection method (Graham et al, supra), followed by plaque purification of the resulting adenovirus particles and propagation thereof on human 293 cells, as described above. The resulting adenovirus mutant was designated "SV5".

The structure of SV5, with a total size of about 35 kb, was confirmed by PCR amplification of the left inverted terminal repeat using primer SEQ ID NO:3 as the forward primer, and 5'-CCGGGTATAAATACACTACACGTC-3' (SEQ ID NO:5), which corresponds to nucleotides 480–457 of the viral genome, as the reverse primer.

The PCR conditions used were: Denaturation at 95° C. for 10 min, followed by 30 cycles of denaturation (95° C. for 1.5 min), annealing (60° C. for 1 min) and extension (72° C. for 2 min), followed by a single extension step at 720 for 10 min.

The structure of SV5 was also confirmed by restriction analysis of SV5 DNA.

EXAMPLE 4

Preparation of Gene Transfer Vector pAdDYSβgal

A gene transfer vector having the Ad5 inverted terminal repeats and packaging signal attached to both ends, and carrying 28.2 kb of foreign DNA that includes a lacZ marker gene encoding *E. coli* β-galactosidase (β-gal) under the control of the cytomegalovirus (CMV) promoter (4.6 kb) (MacGregor et al, *Nucl. Acid. Res.*, 17:2365 (1989)), and the full-length murine dystrophin cDNA (13.8 kb) (Lee et al, *Nature,* 349:334 (1991)) under the control of a large muscle-specific (MCK) promoter (6.5 kb) that includes the first intron and that is active only in skeletal and cardiac muscle (Jaynes et al, *Mol. Cell. Biol.*, 6:2855 (1986); and Cox et al, *Nature,* 364:725 (1993)), was prepared as follows:

A. Preparation of pDYSβgal 1.8 μg of 13luescript II KS was digested with EcoRV. 100 ng of the resulting digested DNA was ligated to 1.0 ng of the following double stranded oligonucleotide: 5'-GGCGCGCCCCTAGGGGCCGGCCTTAATTAA-3' (SEQ ID NO:6), which was produced by chemical synthesis (Sambrook et al, supra), using T4 DNA ligase (Sambrook et al, supra). This oligonucleotide contains the following restriction endonuclease recognition sequences: AscI, AvrII, FseI, PacI. The resulting plasmid was called pSTK2.

Then, 1.0 μg of pSTK2 was digested with BstxI, and the cleavage site was made blunt end using Klenow enzyme, as described by Sambrook et al, supra.

Next, 80 ng of the resulting digested pSTK2 was ligated to 5.0 ng of the following doubled stranded oligonucleotide: 5'-ATTTAAATGCCCGCCCGTTTAAACTACGTA-3' (SEQ ID NO:7), which was produced by chemical synthesis (Sambrook et al, supra), using T4 DNA ligase (Sambrook et al, supra). This oligonucleotide has the following restriction endonuclease recognition sequences: SwaI, SrfI, PmeI, SnaBI. The resulting plasmid was called pSTK3.

Then, 3.2 μg of pSTK3 was digested with ClaI, and the cleavage site was made blunt end using 3.0 units of Klenow enzyme and 0.5 μl of 10 mM of each desoxynucleotide triphosphate (dNTP) in a 50 μl reaction volume. 100 ng of the resulting product was ligated to 10 ng of a 298 bp XhoI-XbaI DNA fragment containing the polyadenylation signal from the bovine growth hormone gene (Sasavage et al, *Biochem.*, 19:1737–1743 (1986)). This fragment was obtained by digestion of pPol2shortneobpA (Soriano et al, *Cell*, 64:693–702 (1991)) with XhoI and XbaI, followed by making both sites blunt using Klenow enzyme and dNTP's, as described above.

Thereafter, 3.6 μg of the resulting plasmid was digested with HincII, followed by dephosphorylation using Calf Intestinal Alkaline Phosphatase (New England Biolabs), as described by Sambrook et al, supra).

Then, 100 ng of the digested DNA was ligated to 200 ng of the 13.8 kb SmaI fragment of pCCL-DMD (Lee et al, *Nature,* 349:334 (1991)). The resulting plasmid was called STK3DMDpolyA.

In a different reaction, STK3 was digested with SmaI, followed by dephosphorylation, as described above. A 4.6 kb EcoRI-SalI DNA fragment was then obtained from pCMVβgal (MacGregor et al, supra) by digestion with EcoRI and SalI, followed by making the ends blunt with Klenow enzyme, as described above, was isolated by 0.8% (w/v) agarose gel electrophoresis and electroelution, as described above.

100 ng of the resulting SmaI-digested STK3 DNA was ligated to 150 ng of the isolated EcoRI-SalI CMVβgal fragment.

3.6 Mg of the resulting plasmid was digested with Sal I, followed by making the ends blunt end using Klenow enzyme, followed by dephosphorylation, as described above.

Then, 100 ng of the resulting digested DNA was ligated to 100 ng of a 14.1 kb XhoI fragment encompassing the 13.8 kb SmaI DMD cDNA fragment and the bovine polyadenylation signal. This fragment was obtained by digesting plasmid STK3DMDpolyA with XhoI, and purified by 0.8% (w/v) agarose gel electrophoresis followed by electroelution, as described above. The resulting plasmid was called STK3DMDpolyACMVβgal.

Figure 5:
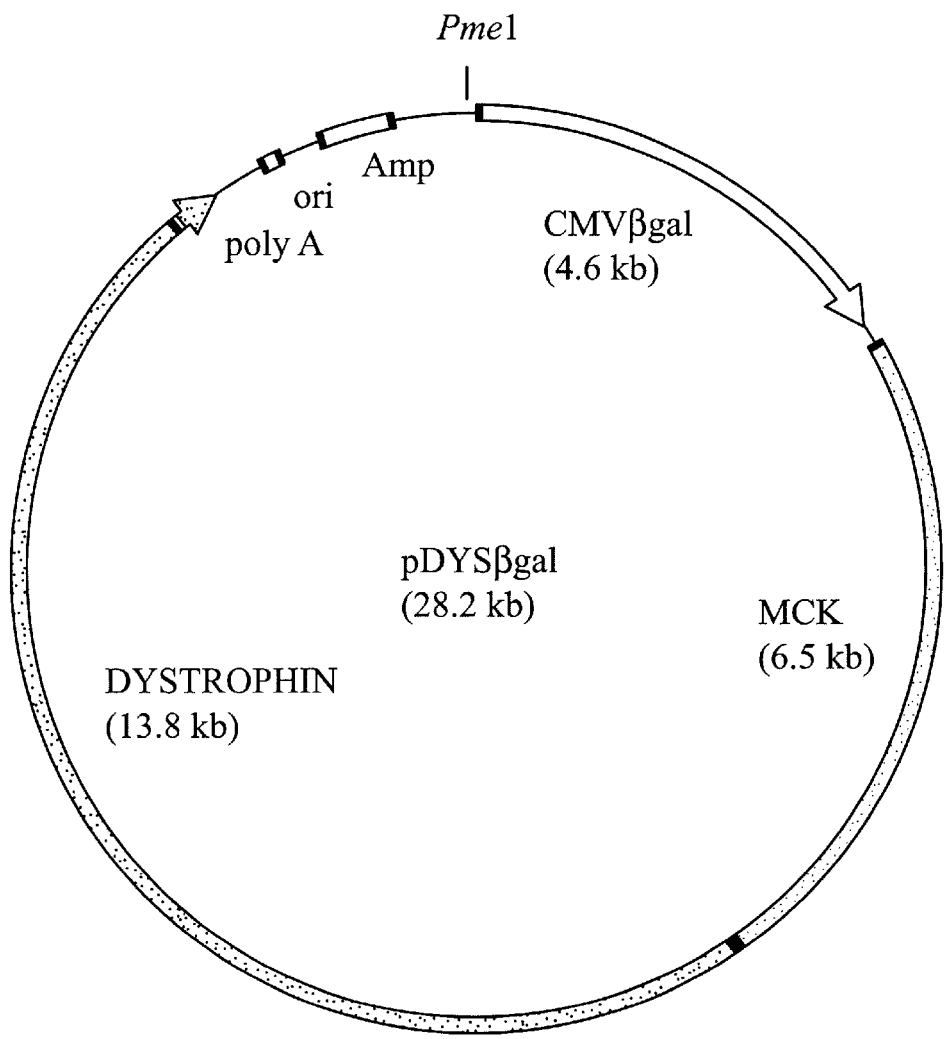
FIG. 5 shows gene transfer vector pDYSβgal, which contains the 6.5 kb murine muscle creatine kinase promoter (MCK), the murine 13.8 kb full-length dystrophin cDNA (dystrophin), the 290 bp polyadenylation signal of the bovine growth hormone gene (polyA), and the 4.6 kb *E. coli lacZ* gene under the control of the early cytomegalovirus promoter (CMVβgal). The bacterial origin of replication (ori) and ampicillin resistance gene (Amp) are also indicated. This plasmid has a unique PmeI restriction site.

Then, 1.0 μg of STK3DMDpolyACMVβgal was digested with AvrII, followed by making the ends blunt with Klenow enzyme, as described above, followed by dephosphorylation, as described above. 100 ng of the resulting digested DNA was ligated to 100 ng of a 6.5 kb XhoI fragment containing the MCK promoter which included the first intron (Jaynes et al, supra), that had been made blunt by using Klenow enzyme, as described above. The resulting plasmid was called pDYSβgal (FIG. 5).

B. Ligation of Adenovirus Termini to pDYSβal 10 ng of Ad5 DNA (Eastman Kodak, New Haven, Conn.) was used as template to amplify the left terminus of Ad5 by PCR. The forward primer used was SEQ ID NO:3, which contains nucleotides 1–25 of the viral genome; and the reverse primer used was SEQ ID NO:5, which corresponds to nucleotides 480–457 of the viral genome.

The PCR conditions used were: Denaturation at 94° C. for 5 min, followed by 30 cycles of denaturation (94° C. for 0.5 min), annealing (50° C. for 0.5 min) and extension (70° C. for 0.5 min), followed by a single extension step at 70° for 5 min.

The resulting 485 bp PCR product was purified using a Magic PCR Prep column (Promega, Madison, Wis.), and the resulting purified DNA was suspended in TE buffer, and made blunt ended with Klenow enzyme in the presence of 60 mM of each dNTP. Unincorporated nucleotides were removed by a Prep-A-Gene kit (BIORAD). The final yield was 1.5 μg.

Next, 50 ng of the resulting PCR product was ligated to 50 ng of pUC18 (New England Biolabs), that had previously been digested with SmaI and dephosphorylated (Sambrook et al, supra). The resulting plasmid was called pITR54. pITR54 contains the left terminus of Ad5, including the complete packaging signal.

6.0 μg of pITR54 was digested with SacII, followed by making the restriction sites blunt using T4 DNA polymerase. Then, the DNA was digested with ApaI. The resulting 358 bp fragment, containing the left inverted terminal repeat and the complete packaging signal, was isolated by 1.5% (w/v) agarose gel electrophoresis. About 400 ng of the DNA was electroeluted as described above.

Separately, 4.0 μg of Bluescript II KS DNA was digested with HindIII, followed by blunt ending with Klenow enzyme, as described above. The resulting DNA was digested with ApaI, and the DNA dephosphorylated with Calf Intestinal Alkaline Phosphatase, as described above.

Thereafter, 20 ng of the purified 358 bp DNA fragment was subcloned into 100 ng of the digested Bluescript DNA using T4 DNA ligase. The resulting plasmid was called pSTK17.

Then, 50 μg of plasmid pSTK17 was digested with ApaI and EcoRV, and the resulting 358 bp ApaI-EcoRV fragment containing the left inverted terminal repeat and the complete packaging signal of Ad5, was isolated by 1.5% (w/v) agarose gel electrophoresis, and electroeluted, as described above.

Figure 6:
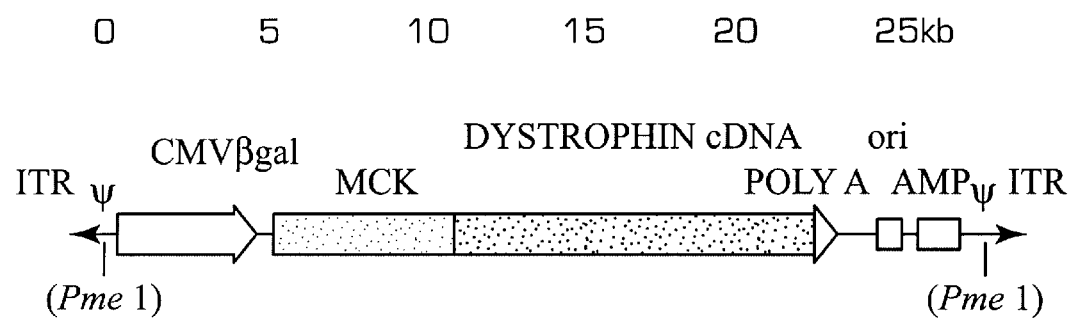
FIG. 6 shows the structure of pAdDYSβgal, which was obtained by linearization of pDYSβgal with PmeI, and ligation of the left terminus of Ad5 containing the inverted terminal repeat (ITR), and the full-length packaging signal (Ψ), to the ends of the linearized DNA using T4 DNA ligase. The PmeI site is destroyed during the ligation step.

4.0 μg of the resulting isolated ApaI-EcoRV DNA fragment was dephosphorylated with CIP, and 5.0 μg of pDYSβgal, which had been linearized with PmeI, was ligated to 500 ng of the resulting dephosphorylated ApaI-EcoRV DNA fragment using T4 DNA ligase in the presence of 100 μM ATP, in order to enhance blunt-end ligation, for 16 hr at room temperature. The resulting ligation product was purified by phenol/chloroform extraction, followed by ethanol precipitation, so as to obtain the gene transfer vector, designated "pAdDYSβgal" (FIG. 6). PAdDYSβgal, which does not contain any the viral coding sequences, has been deposited at the American Type Culture Collection on Jun. 7, 1995, under ATCC No. 97205.

EXAMPLE 5

Production of Recombinant Adenovirus AdDYSβgal

A. Preparation of SV5 Genomic DNA

SV5 genomic DNA was prepared as a DNA/terminal protein complex as follows:

SV5 obtained in Example 3 was propagated on human 293 cells, and a 500 μl cell extract was prepared from a single 150 mm monolayer containing $1.0 \times 10^7$ human 293 cells by three freeze/thaw cycles. The SV5 genomic DNA, which retains the terminal protein attached at the termini, was freed from the virus capsids by incubating the resulting SV5 freeze/thaw extract with an equal volume of extraction buffer comprising 8.0 M guanidine hydrochloride, 10 mM Tris-HCl (pH 7.5), 2.0 mM EDTA and 4.0 mM β-mercaptoethanol, at 4° C. for 20 min.

8.0 μl of the resulting SV5 genomic DNA/terminal protein complex was co-transfected with 5.0 μg of the pAdDYSβgal gene transfer vector obtained in Example 4, which has the adenovirus termini ligated to both ends, into 80% confluent human 293 cells grown in MEM medium containing 10% (v/v) newborn calf serum using the calcium phosphate transfection method (Graham et al, supra). The transfection efficiency was approximately 100-fold higher than with DNA without the terminal protein attached. After a 5 hr incubation at 37° C., the medium was changed, and after another 12 hr of incubation at 37° C., the resulting cell monolayers were overlaid with 10 ml of 0.5% (w/v) agarose containing MEM medium supplemented with 5.0% (v/v) newborn calf serum. Approximately 50–100 plaques per 60 mm dish (about $1.5 \times 10^6$ human 293 cells per 60 mm cell culture dish) were obtained.

Individual plaques were isolated after 5–7 days, and resuspended in 250 μl of $PBS^{2+}$ containing 10% (v/v) glycerol, and subjected to a single freeze-thaw cycle.

30 μl of the resulting suspension was used to infect confluent monolayers of COS-7 cells plated in 24 mm dishes on the previous day, as described by Mitani et al, supra. 16 hr post-infection at 37° C., the COS-7 cells were fixed with 0.5% (v/v) glutaraldehyde in PBS, and stained with X-gal as described by MacGregor et al, supra; and Mitani et al, supra.

Those plaque isolates giving a higher number of β-gal expressing COS-7 cells were isolated, and used to infect $1.0 \times 10^4$ human 293 cells per well in 24 well dishes using 150 μl of the primary plaque isolate suspension for infection. 48 hr post-infection, the cells were harvested, as described above, and cell extract was prepared as described above. The resulting cell extract was used to infect $1.0 \times 10^5$ human 293 cells plated in 6 well dishes. 48 hr post-infection, a cell extract was prepared, as described above, and used to infect $1.0 \times 10^6$ human 293 cells plated in 60 mm dishes. This procedure of infecting human 293 cells in 60 mm dishes with $1.0 \times 10^6$ human 293 cells per dish was repeated three times. Then, $6.0 \times 10^6$ human 293 cells were infected with the resulting extract. Next, $4.0 \times 10^7$ human 293 cells were infected with extract prepared from the $6.0 \times 10^6$ human 293 cells, as described above. From these $4.0 \times 10^7$ cells, a freeze/thaw extract was prepared that was obtained by first collecting the infected $4.0 \times 10^7$ human 293 cells, resuspending the cells in 4.0 ml of $PBS^{2+}$ containing 5.0% (v/v) glycerol, and then freezing and thawing the sample three times, as described above.

Next, the resulting adenovirus particles, which were a mixture of SV5 particles and recombinant adenovirus particles having encapsidated therein the pAdDYSβgal gene transfer vector, were purified by CsCl equilibrium centrifugation.

More specifically, the cell extract was mixed with 0.5 g of CsCl per ml extract. This resulted in a total volume of about 5.0 ml. 5.0 ml of a 50% (w/v) CsCl solution prepared in $PBS^{2+}$ was added thereto in a centrifugation tube, resulting in a total volume of 10 ml. This sample was centrifuged at 175,587×g at $r_{max}$ for approximately 20 hr at 4° C. in a SW41 rotor. Two distinct bands were visible in the middle of the centrifugation tube after the centrifugation run.

The upper band was isolated by puncturing the centrifugation tube from the side with a needle, followed by collecting the band in a syringe in a total volume of 350 μl. Then, the recombinant adenovirus particles were further purified by additional two CsCl centrifugations under the same conditions.

After CsCl equilibrium centrifugation, 20 μl of the purified particles from the upper and the lower band, respectively, were incubated in a buffer comprising 50 mM Tris-HCl (pH 7.5), 20 mM EDTA, 0.5% (w/v) SDS and 200 μg/ml Proteinase K in a final volume of 400 μl at 37° C. for 4 hr, followed by phenol/chloroform extraction and ethanol precipitation. The resulting DNA was resuspended in 20 μl of TE buffer. A 10 μl aliquot was then digested with BamHI according to the manufacturer's recommendation (Boehringer Mannheim), followed by 0.8% (w/v) agarose gel electrophoresis, where ethidium bromide was included in the agarose gel at a concentration of 100 ng/ml. The DNA bands were visualized under UV light at a wavelength of 254 nm, and the result was documented using a video camera gel documentation system (UVP, San Gabriel, Calif.).

Southern blot analysis (Southern, *J. Mol. Biol.*, 98:503 (1975) was carried out using the resulting gel and 5.0 ng of $^{32}$P-labeled pDYSβgal DNA or Ad5 DNA as the probe. The probes were prepared as described by Feinberg et al, *Anal. Biochem.*, 132:6 (1983). Pre-hybridization and hybridization were performed in 1.5× SSPE containing 1.0% (w/v) SDS, 1.0% (v/v) nonfat milk and 20% (w/v) dextran sulfate at 65° C. for 12–16 hr. 20× SSPE comprises 3.0 M NaCl, 0.5 M NaH$_2$PO$_4$ and 2.0 mM EDTA (pH 7.4). The membranes were washed twice for 15 min with 2× SSC containing 0.5% (w/v) SDS. 20× SSC comprises 3.0 M NaCl and 0.3 M Na-Citrate. Next, the membranes were washed three times for 20 min with 0.1× SSC containing 0.5% (w/v) SDS at 65° C., followed by exposure to X-omat AR X-ray films for 1–12 hr.

0.3 μl aliquots of the resuspended DNA were also digested with BamHI, HindIII, PvuII, XbaI, or NotI, and subjected to Southern blot analysis using either 25 ng of $^{32}$P-labeled pDYSβgal DNA or 25 ng of the 358 bp left terminal SacI fragment of Ad5 as probes.

These experiments confirmed that the overall structure of pDYSβgal had been preserved during the rescue of AdDYSβgal, with the viral left terminal DNA linked to the PmeI sites of the linearized pDYSβgal.

Plaque assays (Graham et al, supra) indicated that the titer of SV5 was $5.0 \times 10^9$/ml in the lower band, and $4.0 \times 10^6$/ml in the upper band. Therefore, the upper band, comprised mainly AdDYSβgal virus particles, and contained approximately 100-fold more "infectious" AdDYSβgal particles than infectious SV5 particles.

The titer of the purified AdDYSβgal virus particles was determined to be $5.0 \times 10^8$/ml by infection of human 293 cells followed by staining with X-gal after 23 hr, as described above.

In the case were the gene transfer vector does not contain a marker gene, then a different method, e.g., PCR, is used to determine which of the primary plaque isolates contains the gene transfer vector.

The resulting isolated plaque is then used for propagation on human 293 cells as described above.

These results demonstrated the successful rescue, amplification and purification of recombinant adenovirus particles having a 28.2 kb foreign DNA insert, and lacking any viral DNA, except for the 358 bp left inverted terminal repeat with the essential elements for viral replication and D packaging.

AdDYSβgal has all of the viral coding sequences removed, thus eliminating expression of all viral proteins and accommodating large inserts. These modifications were designed to reduce the host immune response to the vector, and to provide for long-term expression of the dystrophin gene.

EXAMPLE 6

Expression of Dystrophin

Expression of dystrophin from AdDYSβgal virus particles obtained in Example 5 was analyzed following infection of primary myoblasts derived from mdx mice. The mdx mice were obtained from a breeding colony maintained at Baylor College of Medicine, Houston, Tex. The founder animals for this colony were obtained from The Jackson Laboratory, Bar Harbor, Me. The mdx mice are a spontaneous mutant, C57BL/10 mdx/mdx, with a nonsense mutation in the dystrophin gene (Sicinski et al, *Science*, 244:1578 (1989), and are a genetic and biochemical model for human DMD disease (Partridge, *Neuropathol. Appl. Neurobiol.*, 17:353 (1991)).

More specifically, primary dystrophin-deficient myoblasts were isolated from skeletal muscle of a 7-day mdx mouse as described by Rando et al, *J. Cell. Biol.*, 125: 1275 (1994). The myoblasts were propagated on collagen-coated dishes in growth medium consisting of Ham's nutrient mixture F-10 supplemented with 20% (v/v) fetal bovine serum, 100 units/ml penicillin G and 100 μg/ml streptomycin. The myoblasts were plated at a density of $2.0 \times 10^5$ cells per 3.5 cm collagen-coated dish, and infected with purified AdDYSβgal virus particles over a range of 2 to 50 m.o.i., as determined by infection of human 293 cells. 24 hr post-infection, the growth medium was replaced with fusion medium comprising DMEM supplemented with 2.0% (v/v) horse serum, $2.5 \times 10^6$ M dexamethasone and $10^{-6}$ M insulin. The fusion medium was changed daily until the cells were stained for β-gal expression or collected for dystrophin expression analysis. Staining 24 hr after infection with X-gal demonstrated prominent β-gal expression.

In parallel, additional myoblast monolayers were induced to differentiate into myotubes 24 hr after infection by the application of fusion medium as described above. Four days after induction of cell fusion, myotubes were stained with X-gal, and found to exhibit very strong expression and accumulation of β-gal in the transduced primary mdx myotubes.

The monolayers infected with AdDYSβgal virus particles were analyzed for dystrophin expression using a Western blot as follows:

The monolayers were rinsed three times with PBS, and three times with buffer comprising 50 mM Tris-HCl (pH 8.0), 5.0 mM EDTA and 5.0 mM EGTA (hereinafter "TEE buffer"). The cells were collected in a small volume of TEE buffer, and centrifuged at 14,000×g for 5 min at 4° C. The resulting cell pellet was resuspended in TEE buffer containing 0.3% (w/v) SDS, and incubated on ice for 20 min. Brief sonication was then carried out to reduced the viscosity of the sample. Total protein concentration was assayed using the bicinchoninic acid protein assay reagent (Pierce, Rockford, Ill.). 25 μg of protein from the sonicated cell pellet were separated by electrophoresis on a 5.0% (w/v) SDS-PAGE gel, and transferred to a nitrocellulose membrane. The membrane was blocked with 5.0% (v/v) nonfat milk and 5.0% (v/v) goat serum in Tris-buffered saline-Tween comprising 20 mM Tris-HCl (pH 8.0), 137 mM NaCl and 0.1% (v/v) polyoxyethylene sorbitan monolaurate (Tween 20) (hereinafter "TBS-T") for 1 hr. Then, immunostaining was performed according to the protocol for ECL Western blotting detection reagents (Amersham Life Science, Buckinghamshire, UK) using DYS2 (Novocastra Laboratories, Newcastle upon Tyne, UK), a mouse monoclonal antibody directed against the carboxy terminal 17 amino acids of dystrophin, diluted 1:100 in TBS-T, as the primary antibody, and horseradish peroxidase-conjugated anti-mouse antibody (Kirkegaard & Perry Laboratories, Gaithersburg, Md.), diluted 1:5000 in TBS-T as the secondary antibody. The chemiluminescent signal was detected by a 30 sec exposure to autoradiography film.

In a parallel experiment, C2C12 myoblasts (ATCC CRL 1772) were plated at a density of $4.0 \times 10^4$ cells per 3.5 cm collagen-coated dish in DMEM growth medium supplemented with 10% (v/v) fetal bovine serum, 100 units/ml penicillin G and 100 μg/ml streptomycin. 48 hr later, lipofection was performed according to the manufacturer's directions using 3.0 μg of pDYSβgal and 10 μl of lipofectamine (Gibco BRL, Gaithersburg, Md.) per dish. Some transfected monolayers were stained with X-gal 24 hr post-transfection, demonstrating β-gal expression in 17% of the myoblasts. Others were switched to fusion medium that was changed daily for 7 days prior to collection for dystrophin protein expression analysis, as described above.

A specific band of 427 kD was detected in primary myotubes transduced by AdDYSβgal virus particles, and in the C2C12 muscle cell line transfected with pDYSβgal, but not in untransduced primary myotubes. Upon comparison with dystrophin expressed in myotubes derived from normal mouse muscle, the transferred dystrophin cDNA was shown to be full-length. These results demonstrated that the dystrophin cDNA, under the control of the MCK promoter, was expressed in primary myotubes fused from myoblasts that were transduced with AdDYSβgal virus particles.

EXAMPLE 7

Expression of Dystrophin and β-gal In Vivo

In vivo expression of dystrophin and β-gal from AdDYSβgal virus particles obtained in Example 5 was analyzed by intramuscular injection of AdDYSβgal virus into the hind limb of the mdx mouse. Again, the mdx mouse is a genetic and biochemical model for human DMD disease (Partridge, supra).

More specifically, 5.0 μl of recombinant AdDYSβgal particles, which had been dialyzed against $PBS^{2+}$ containing 5.0% (v/v) glycerol ($2.5 \times 10^6$ virus particles in total), were injected percutaneously in the right distal posterior hind limb of 3–5 day old mdx mice. As a control, the left distal posterior hind limb of each animal was injected percutaneously with 5.0 μl of $PBS^{2+}$ containing 5.0% (v/v) glycerol. Ten to fifteen days post-injection, the gastrocnemius and anterior tibial muscles were collected by surgical removal after sacrificing the animal, then frozen in liquid nitrogen-cooled isopentane, and then sectioned using a cryomicrotome at 6.0 μm thickness. Next, the muscle sections were either stained for β-gal or immunostained for dystrophin.

More specifically, sections for β-gal staining were fixed for 5 min with 2.0% (v/v) formaldehyde and 0.2% (v/v) glutaraldehyde in PBS, and then stained for 6–12 hrs at 37° C. with X-gal stain comprising 5.0 mM potassium ferricyanide, 5.0 mM potassium ferrocyanide, 2.0 mM magnesium chloride, and 0.1% (w/v) X-gal in PBS. β-gal-stained sections were counterstained with hematoxylin and eosin (Lillie, In: *H.J. Conn's Biological Stains*, 9th ed., Williams and Wilkins Co., Baltimore, Md., pp. 342 (1977)).

Dystrophin immunostaining was carried out on unfixed sections by first blocked with blocking solution comprising PBS containing 10% (v/v) goat serum and 2.0% (w/v) bovine serum albumin, and then, using affinity purified anti-dystrophin antibody d10 (Hoffman et al, *Lancet*, ii:1211 (1989); Hoffman et al, *J. Neurol. Sci.*, 99:9 (1990); and Koenig et al, *J. Biol. Chem.*, 265:4560 (1990)) diluted 1:250 in blocking solution as the primary antibody, and FITC-conjugated donkey anti-sheep antibody (Jackson Immunoresearch Laboratories) diluted 1:1000 in blocking solution as the secondary antibody. The sections immunostained for dystrophin were then mounted in a glycerol-based medium containing 1.0 mg/ml paraphenylenediamine, and viewed with a Zeiss Axiophot microscope equipped for fluorescence microscopy.

Serial sections of injected muscles demonstrated regional dual expression of β-gal and dystrophin. The intensity of dystrophin immunostaining at the muscle membrane was homogeneous within each expressing fiber, but the level of expression varied between fibers. The level of dystrophin at the muscle membrane of fibers with the highest level of expression was nearly the same as that seen in normal mouse muscle. All dystrophin expression was properly localized to the sarcolemma. Hematoxylin and eosin staining of serial sections demonstrated no difference in histopathology between injected and control muscles, or between expressing or non-expressing regions of the injected muscle.

The ultimate goal of somatic gene transfer for DMD and BMD is correction of the sarcolemmal defect that leads to muscle degeneration. Transgenic mdx mouse lines expressing the dystrophin cDNA in cardiac and skeletal muscle (Lee et al, *Hum. Gene Ther.*, 4:159 (1993); and Cox et al, *Nature*, 364:725 (1993)), provide a germ-line gene correction model for demonstrating that the functional defect in mdx mice can be corrected by gene transfer of the dystrophin cDNA. The dystrophin construct under the control of the MCK promoter in these transgenic studies is nearly identical to that in AdDYSβgal. Therefore, a sufficient level of somatic gene transfer using AdDYSβgal virus particles should result in functional correction of the cytoskeletal defect in DMD.

While the invention has been described in detail, and with reference to specific embodiments thereof, it will be apparent to one of ordinary skill in the art that various changes and modifications can be made therein without departing from the spirit and scope thereof.

What is claimed:

1. A method for treatment of muscular dystrophy comprising,
   infecting muscle cells of a subject in need of such treatment with a recombinant adenovirus particle which has encapsidated therein a gene transfer vector consisting essentially of the following elements, in 5' to 3' orientation:
   (i) a first adenovirus inverted terminal repeat,
   (ii) a gene encoding full-length dystrophin operably linked to a promoter functional in muscle cells, and
   (iii) a second adenovirus inverted terminal repeat,
   wherein one or both of elements (i) and (iii) additionally comprise an adenovirus packaging signal,
   wherein said infecting results in expression of dystrophin, and correction of cytoskeletal defects that lead to muscular dystrophy.

2. The method of claim 1 wherein said promoter is the murine muscle creatine kinase promoter.

* * * * *